United States Patent
Lau et al.

(10) Patent No.: US 8,962,015 B2
(45) Date of Patent: Feb. 24, 2015

(54) ORALLY BIOAVAILABLE LIPID-BASED CONSTRUCTS

(75) Inventors: John R. Lau, Howard, OH (US); W. Blair Geho, Wooster, OH (US)

(73) Assignee: SDG, Inc., Cleveland, OH (US)

( * ) Notice: Subject to any disclaimer, the term of this patent is extended or adjusted under 35 U.S.C. 154(b) by 378 days.

(21) Appl. No.: 11/904,937

(22) Filed: Sep. 28, 2007

(65) Prior Publication Data

US 2009/0087479 A1 Apr. 2, 2009

(51) Int. Cl.
*A61K 9/127* (2006.01)
*A61K 38/28* (2006.01)
*A61P 3/00* (2006.01)

(52) U.S. Cl.
CPC .............. *A61K 38/28* (2013.01); *A61K 9/127* (2013.01)
USPC ............................. 424/450; 514/1.1; 514/5.9

(58) Field of Classification Search
None
See application file for complete search history.

(56) References Cited

U.S. PATENT DOCUMENTS

| | | | |
|---|---|---|---|
| 4,603,044 A | | 7/1986 | Geho et al. |
| 4,740,375 A | * | 4/1988 | Geho et al. ................. 424/450 |
| 4,946,787 A | | 8/1990 | Eppstein et al. |
| 5,104,661 A | | 4/1992 | Lau |
| 5,567,432 A | | 10/1996 | Lau et al. |
| 6,063,400 A | * | 5/2000 | Geho et al. ................. 424/450 |
| 6,726,924 B2 | | 4/2004 | Keller |
| 7,169,410 B1 | * | 1/2007 | Lau et al. ................... 424/450 |
| 2003/0133972 A1 | * | 7/2003 | Danthi et al. .............. 424/450 |
| 2005/1002682 | | 2/2005 | Hoenig |
| 2006/0222697 A1 | * | 10/2006 | Lau et al. ................... 424/450 |
| 2006/0222698 A1 | * | 10/2006 | Lau et al. ................... 424/450 |
| 2007/0104777 A1 | * | 5/2007 | Lau et al. ................... 424/450 |
| 2007/0218117 A1 | | 9/2007 | Lau et al. |

FOREIGN PATENT DOCUMENTS

| | | |
|---|---|---|
| WO | WO 99/59545 | 11/1999 |
| WO | WO 2006/127361 | 11/2006 |
| WO | WO 2009/042945 | 4/2009 |

OTHER PUBLICATIONS

Walde et al., Biomolecular Engineering, 18 (2001) 143-177.*
Erion, et al., "Targeting thyroid hormone receptor-β agonists to the liver reduces cholesterol and triglycerides and improves the therapeutic index," *PNAS*, Sep. 25, 2007, 104(39):15490-15495.
Dong, C. et al., "Acacia-Gelatin Microencapsulated Liposomes: Preparation, Stability, and Release of Acetylsalicylic Acid," Pharmaceutical Research, 1993, pp. 141-146, vol. 10, No. 1.
Extended European Search Report dated Dec. 21, 2012 for copending European Application No. 08834499.9.

* cited by examiner

*Primary Examiner* — Doug Schultz
(74) *Attorney, Agent, or Firm* — Saul Ewing LLP; Kathryn Doyle; Domingos J. Silva

(57) ABSTRACT

The present invention is embodied by a composition capable of chaperoning a typically non-orally available therapeutic or diagnostic agent through the environment of the digestive tract such that the therapeutic or diagnostic agent is bioavailable. The composition may or may not be targeted to specific cellular receptors, such as hepatocytes. Therapeutic agents include, but are not limited to, insulin, calcitonin, serotonin, and other proteins. Targeting is accomplished with biotin or metal based targeting agents.

2 Claims, 11 Drawing Sheets

ORAL ABSORPTION OF COMPOSITION FROM NORMAL RATS DRINKING WATER

ORALLY BIOAVAILABLE LIPID-BASED CONSTRUCTS

BACKGROUND OF THE INVENTION

One of the most preferred ways to deliver a pharmaceutical to a subject is in an oral formulation. However, oral formulations of many pharmaceutical compounds are often unavailable due to the pharmaceutical's incompatibility with the harsh environment of the digestive tract. This is particularly true for pharmaceutical compounds such as peptides, proteins, certain small molecules, and nucleic acids.

An oral formulation of a protein such as insulin would be highly desirable. Present strategies to normalize blood glucose levels in Type I and Type II diabetic patients utilize subcutaneous administration of insulin in various time-released formulations, such as ultralente and humulin NPH insulin. Use of these formulations delay and subsequently control the bio-distribution of insulin by regulating release of the drug to tissues. Sustained management of insulin leads to better glucose control and the need for fewer injections over the course of the disease. Unfortunately, multiple painful injections are still required because these formulations fail to provide sustained levels of insulin in the subject suffering from diabetes.

Many other important drugs are also not presently available in oral formulations. Examples include calcitonin, serotonin, parathyroid hormone, GLP-1, erythropoietin, interferon of various types, human growth hormone, and monoclonal antibodies, the utilities of which have been extensively reviewed in the literature.

What is needed in the field of oral drug delivery is a composition that enables oral delivery of a wide range of pharmaceutical products. The present invention meets and addresses this need.

BRIEF SUMMARY OF THE INVENTION

The present invention includes compositions that facilitate and/or enable absorption of therapeutics which are not typically orally bioavailable. In one embodiment, a composition of the invention functions by associating with a therapeutic agent and chaperoning the therapeutic agent through the lumen of the gut into the portal blood flow and finally on to the systemic circulation. In certain embodiments, the composition of the invention possess many unique and advantageous properties. One of these properties is the ability to insert into intercellular gaps and pass through the mammalian gut into the portal circulation. In certain embodiments, a composition of the invention may be targeted to specific cellular or extracellular receptors via one or more targeting agents.

In a typical embodiment, an orally bioavailable composition of the invention comprises gelatin and additional constituents. The additional constituents comprise a dynamically sized liposome, liposome fragment, and lipid particle, wherein the lipid particle comprises at least one lipid component and the liposome or liposome fragment comprise at least two lipid components. The composition further comprises at least one therapeutic or diagnostic agent and, optionally, at least one targeting agent. Preferably, the gelatin actively reversibly interacts with one or more of the constituents.

In certain embodiments, the lipid components are selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), and triethylammonium 2,3-diacetoxypropyl 2-(5-((3aS,6aR)-2-oxohexahydro-1H-thieno[3,4-d]imidazol-4-yl)pentanamido)ethyl phosphate.

In certain embodiments, the therapeutic agent is a cellular metabolic regulator.

In certain embodiments, the targeting agent comprises a metal-derived targeting agent or a biotin-derived targeting agent.

In one sub-embodiment, the metal-derived targeting agent comprises a metal and at least one complexing agent. Preferably, the metal in the metal-derived targeting agent is selected from the group consisting of a transition metal, an inner transition metal and a neighbor of the transition metal, and, the at least one complexing agent is selected from the group consisting of:

N-(2,6-diisopropylphenylcarbamoylmethyl)iminodiacetic acid;
N-(2,6-diethylphenylcarbamoylmethyl)iminodiacetic acid;
N-(2,6-dimethylphenylcarbamoylmethyl)iminodiacetic acid;
N-(4-isopropylphenylcarbamoylmethyl)iminodiacetic acid;
N-(4-butylphenylcarbamoylmethyl)iminodiacetic acid;
N-(2,3-dimethylphenylcarbamoylmethyl)iminodiacetic acid;
N-(2,4-dimethylphenylcarbamoylmethyl)iminodiacetic acid;
N-(2,5-dimethylphenylcarbamoylmethyl)iminodiacetic acid;
N-(3,4-dimethylphenylcarbamoylmethyl)iminodiacetic acid;
N-(3,5-dimethylphenylcarbamoylmethyl)iminodiacetic acid;
N-(3-butylphenylcarbamoylmethyl)iminodiacetic acid;
N-(2-butylphenylcarbamoylmethyl)iminodiacetic acid;
N-(4-tertiary butylphenylcarbamoylmethyl)iminodiacetic acid;
N-(3-butoxyphenylcarbamoylmethyl)iminodiacetic acid;
N-(2-hexyloxyphenylcarbamoylmethyl)iminodiacetic acid;
N-(4-hexyloxyphenylcarbamoylmethyl)iminodiacetic acid;
aminopyrrol iminodiacetic acid;
N-(3-bromo-2,4,6-trimethylphenylcarbamoylmethyl)iminodiacetic acid;
benzimidazole methyl iminodiacetic acid;
N-(3-cyano-4,5-dimethyl-2-pyrrylcarbamoylmethyl)iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl)iminodiacetic acid.

In an embodiment, the metal is chromium.

In an another embodiment of the invention, the metal-derived targeting agent is poly[Cr-bis(N-2,6-diisopropylphenylcarbamoylmethyl iminodiacetic acid)].

In still another embodiment, the targeting agent is a biotin-derived targeting agent selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE; biotin-X-DHPE; 12-((biotinyl)amino)dodecanoic acid; 12-((biotinyl) amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl)ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and 1,2-dipalmitoyl-sn-glycero-3-phosphoethanolamine-N-(biotinyl), iminobiotin derivatives of the aforementioned compounds, and mixtures thereof.

In another sub-embodiment of the invention, the targeting agent is poly[Cr-bis(N-2,6-diisopropylphenylcarbamoylmethyl iminodiacetic acid)] and the therapeutic agent is insulin.

In still another sub-embodiment, the targeting agent is biotin DHPE or biotin-X-DHPE and the therapeutic agent is insulin.

The present invention also describes a method of making an orally bioavailable composition comprising gelatin and additional constituents, where the constituents comprise a dynamically sized liposome, liposome fragment, and a particle, wherein the liposome, liposome fragment, and particle are generated from a mixture of lipid components, the composition further comprising at least one therapeutic or diagnostic agent and, optionally, at least one targeting agent, wherein the gelatin actively reversibly interacts with one or more of the constituents. The method comprises the steps of mixing the lipid components and, optionally, the at least one targeting agent in aqueous media to form a first mixture; adding the therapeutic or diagnostic agent to the first mixture to form a second mixture; adding the second mixture to gelatin to form a gelatin-associated mixture; and drying the gelatin-associated mixture.

In a sub-embodiment of the method, the lipid components are selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), and triethylammonium 2,3-diacetoxypropyl 2-(5-((3aS,6aR)-2-oxohexahydro-1H-thieno[3,4-d]imidazol-4-yl)pentanamido)ethyl phosphate; and when present, the optional targeting agent is a metal-derived targeting agent or a biotin-derived targeting agent; and the therapeutic agent is a cellular metabolic regulator.

In another sub-embodiment of the method of making the orally bioavailable composition of the invention, the metal-derived targeting agent is poly[Cr-bis(N-2,6-diisopropylphenylcarbamoylmethyl iminodiacetic acid)].

In another sub-embodiment of the method of making the orally bioavailable composition of the invention, the biotin derived targeting agent is selected from the group consisting of biotin DHPE and biotin-X-DHPE.

According to another sub-embodiment of the invention, the cellular metabolic regulator is insulin.

The present invention also contemplates a method of treating a disease in a human, the method comprising administering to the human an orally bioavailable composition comprising gelatin and additional constituents, where the constituents comprise a dynamically sized liposome, liposome fragment, and lipid particle, and where the lipid particle comprises at least one lipid component and the liposome or liposome fragment comprises at least two lipid components, and where the composition further comprises at least one therapeutic agent and, optionally, at least one targeting agent, wherein the gelatin actively reversibly interacts with one or more of the constituents.

In a sub-embodiment of the method for treating disease, the disease is diabetes; the lipid components are selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), and triethylammonium 2,3-diacetoxypropyl 2-(5-((3aS,6aR)-2-oxohexahydro-1H-thieno[3,4-d]imidazol-4-yl)pentanamido)ethyl phosphate; the at least one or more therapeutic agents is a cellular metabolic regulator; and when present, the optional targeting agent is a metal-derived targeting agent or a biotin-derived targeting agent.

In a further sub-embodiment, the cellular metabolic regulator is insulin.

In still another sub-embodiment, wherein the targeting agent is not optional, the targeting agent is is poly[Cr-bis(N-2,6-diisopropylphenylcarbamoylmethyl iminodiacetic acid)], biotin DHPE, or biotin-X-DHPE.

In a preferred embodiment of the composition, the lipid components are 1,2 distearoyl-sn-glycero-3-phosphocholine, dihexadecyl phosphate, and cholesterol; the targeting agent is not optional and is poly[Cr-bis(N-2,6-diisopropylphenylcarbamoylmethyl iminodiacetic acid)]; and the therapeutic agent is insulin.

In another preferred embodiment, the lipid components are 1,2 distearoyl-sn-glycero-3-phosphocholine, dihexadecyl phosphate, and cholesterol; the targeting agent is not optional and is biotin-X-DHPE or biotin DHPE; and the therapeutic agent is insulin.

In a preferred embodiment of a method of the invention, the lipid components are 1,2 distearoyl-sn-glycero-3-phosphocholine, dihexadecyl phosphate, and cholesterol; the targeting agent is not optional and is poly[Cr-bis(N-2,6-diisopropylphenylcarbamoylmethyl iminodiacetic acid)]; and the therapeutic agent is insulin.

In another preferred embodiment of the invention, the lipid components are 1,2 distearoyl-sn-glycero-3-phosphocholine, dihexadecyl phosphate, and cholesterol; the targeting agent is not optional and is biotin-X-DHPE or Biotin DHPE; and the therapeutic agent is insulin.

In another aspect of the invention, a composition of the invention may be made by a method comprising the steps of a) mixing at least three lipid components and, optionally, at least one targeting agent in aqueous media to form a first mixture wherein the lipid components are selected from the group consisting 1,2-distearoyl-sn-glycero-3-phosphocholine, 1,2-dipalmitoyl-sn-glycero-3-phosphocholine, 1,2- dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), and triethylammonium 2,3-diacetoxypropyl 2-(5-((3aS,6aR)-2-oxohexahydro-1H-thieno[3,4-d]imidazol-4-yl)pentanamido)ethyl phosphate; b) subjecting the mixture to homogenization to form a mixture of liposomes, liposome fragments, and particles; c) adding a therapeutic or diagnostic agent to the mixture of liposomes, liposome fragments, and particles to create a second mixture; c) adding the second mixture to gelatin to form a gelatin-associated mixture, and; d) drying said gelatin-associated mixture.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

Definitions

Figure 1:
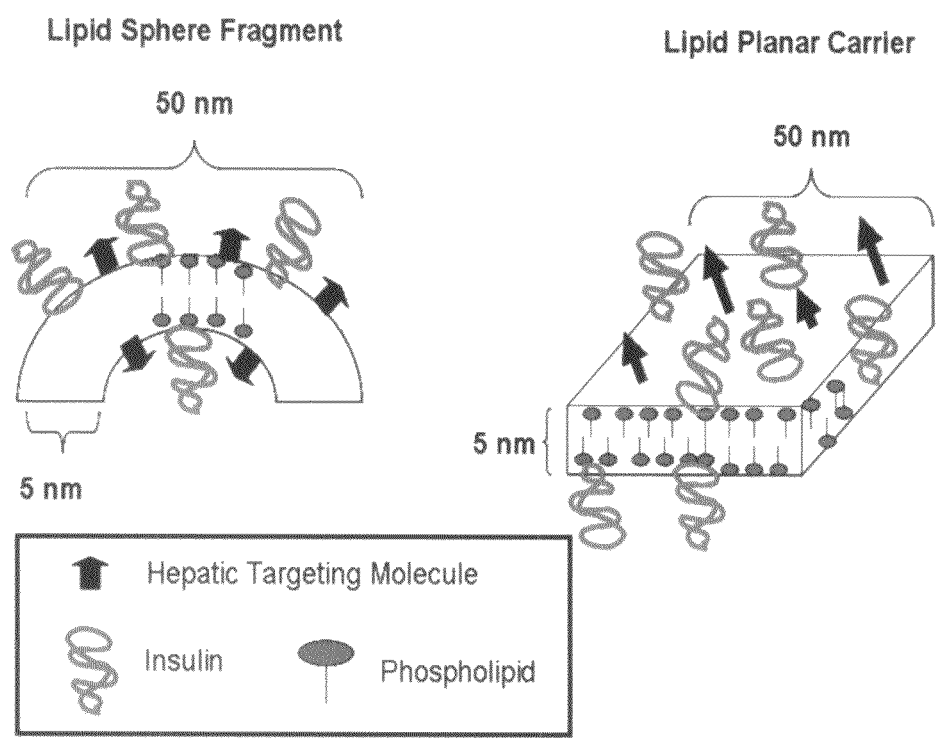
FIG. 1 is a schematic representation of a composition of the invention.

Unless defined otherwise, all technical and scientific terms used herein generally have the same meaning as commonly understood by one of ordinary skill in the art to which the invention belongs. Generally, the nomenclature used herein and the laboratory procedures in organic chemistry and protein chemistry are those well known and commonly employed in the art.

The articles "a" and "an" are used herein to refer to one or to more than one (i.e. to at least one) of the grammatical object of the article. By way of example, "an element" means one element or more than one element.

As used herein, amino acids are represented by the full name thereof, by the three-letter code as well as the one-letter code corresponding thereto, as indicated in the following table:

| Full Name | 3 Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "lower", when used in reference to a chemical structure, describes a group containing from 1 to 6 carbon atoms.

The term "alkyl", by itself or as part of another substituent means, unless otherwise stated, a straight, branched or cyclic hydrocarbon having the number of carbon atoms designated (i.e. $C_1$-$C_6$ means one to six carbons). Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$) alkyl, particularly ethyl, methyl and isopropyl.

The term "alkylene", by itself or as part of another substituent means, unless otherwise stated, a straight, branched or cyclic chain hydrocarbon having two substitution sites, e.g., methylene(—$CH_2$—), ethylene(—$CH_2CH_2$—), isopropylene(—C($CH_3$)=CH—), etc.

The term "aryl", employed alone or in combination with other terms, means, unless otherwise stated, a carbocyclic structure, with or without saturation, containing one or more rings (typically one, two or three rings) wherein said rings may be attached together in a pendant manner, such as a biphenyl, or may be fused, such as naphthalene. Examples include phenyl, anthracyl, and naphthyl. The structure may be optionally substituted with one or more substituents, independently selected from halogen; ($C_1$-$C_6$)alkyl; ($C_1$-$C_6$)alkenyl; ($C_1$-$C_6$)alkoxy; OH; $NO_2$; C≡N; C(=O)O($C_1$-$C_3$) alkyl; ($C_2$-$C_6$)alkylene-$OR^2$; phosphonato; $NR^2_2$; NHC (=O)($C_1$-$C_6$)alkyl; sulfamyl; carbamyl; OC(=O)($C_1$-$C_3$) alkyl; O($C_2$-$C_6$)alkylene-N(($C_1$-$C_6$)alkyl)$_2$; and ($C_1$-$C_3$) perfluoroalkyl.

The term "arylloweralkyl" means a functional group wherein an aryl group is attached to a lower alkylene group, e.g., —CH$_2$CH$_2$-phenyl.

The term "alkoxy" employed alone or in combination with other terms means, unless otherwise stated, an alkyl group or an alkyl group containing a substituent such as a hydroxyl group, having the designated number of carbon atoms connected to the rest of the molecule via an oxygen atom, such as, for example, —OCH(OH)—, —OCH$_2$OH, methoxy (—OCH$_3$), ethoxy (—OCH$_2$CH$_3$), 1-propoxy (—OCH$_2$CH$_2$CH$_3$), 2-propoxy(isopropoxy), butoxy(—OCH$_2$CH$_2$CH$_2$CH$_3$), pentoxy(—OCH$_2$CH$_2$CH$_2$CH$_2$CH$_3$), and the higher homologs and isomers.

The term "acyl" means a functional group of the general formula —C(=O)—R, wherein —R is hydrogen, alkyl, amino or alkoxy. Examples include acetyl (—C(=O)CH$_3$), propionyl(—C(=O)CH$_2$CH$_3$), benzoyl(—C(=O)C$_6$H$_5$), phenylacetyl(C(=O)CH$_2$C$_6$H$_5$), carboethoxy(—CO$_2$CH$_2$CH$_3$), and dimethylcarbamoyl (C(=O)N(CH$_3$)$_2$).

The terms "halo" or "halogen" by themselves or as part of another substituent mean, unless otherwise stated, a fluorine, chlorine, bromine, or iodine atom.

The term "heterocycle" or "heterocyclyl" or "heterocyclic" by itself or as part of another substituent means, unless otherwise stated, a saturated or unsaturated, stable, mono or multicyclic ring system comprising carbon atoms and at least one heteroatom selected from the group comprising N, O, and S, and wherein the nitrogen and sulfur heteroatoms may be optionally oxidized, and the nitrogen atom may be optionally quaternized. Examples include pyridine, pyrrole, imidazole, benzimidazole, phthalein, pyridenyl, pyranyl, furanyl, thiazole, thiophene, oxazole, pyrazole, 3-pyrroline, pyrrolidene, pyrimidine, purine, quinoline, isoquinoline, carbazole, etc. Where substitution will result in a stable compounds, the structure may be optionally substituted with one or more substituents, independently selected from halogen; (C$_1$-C$_6$)alkyl; (C$_1$-C$_6$)alkenyl; (C$_1$-C$_6$)alkoxy; OH; NO$_2$; C≡N; C(=O)O(C$_1$-C$_3$)alkyl; (C$_2$-C$_6$)alkylene-OR$^2$; phosphonato; NR$^2_2$; NHC(=O)(C$_1$-C$_6$)alkyl; sulfamyl; carbamyl; OC(=O)(C$_1$-C$_3$)alkyl; O(C$_2$-C$_6$)alkylene-N((C$_1$-C$_6$)alkyl)$_2$; and (C$_1$-C$_3$)perfluoroalkyl.

The term "amphipathic lipid" means a lipid molecule having a polar end and a non-polar end.

A "complexing agent" is a compound capable of forming a water insoluble coordination complex with a metal, e.g. a salt of chromium, zirconium, etc., that is substantially insoluble in water and soluble in organic solvents.

"Aqueous media" means media comprising water or media comprising water containing at least one buffer or salt.

The terms "associated," or "associated with" when used in reference to a composition or constituent of a composition of the invention, means that the referenced material is incorporated (or intercalated) into, or on the surface of, or within a composition or a constituent of a composition of the present invention.

The term "insulin" refers to natural or recombinant forms of insulin, and derivatives of the aforementioned insulins. Examples of insulin include, but are not limited to insulin lispro, insulin aspart, regular insulin, insulin glargine, insulin zinc, human insulin zinc extended, isophane insulin, human buffered regular insulin, insulin glulisine, recombinant human regular insulin, ultralente insulin, humulin NPH insulin, and recombinant human insulin isophane. Also included are animal insulins, such as bovine or porcine insulin.

The terms "glargine" and "glargine insulin" both refer to a recombinant human insulin analog which differs from human insulin in that the amino acid asparagine at position A21 is replaced by glycine and two arginines are added to the C-terminus of the B-chain. Chemically, it is 21A-Gly-30Ba-L-Arg-30Bb-L-Arg-human insulin and has the empirical formula C$_{267}$H$_{404}$N$_{72}$O$_{78}$S$_6$ and a molecular weight of 6063.

The term "recombinant human insulin isophane" refers to a human insulin that has been treated with protamine.

The term "bioavailability" refers to a measurement of the rate and extent that a pharmaceutical agent, such as, but not limited to, insulin, reaches the systemic circulation and is available at its site of action.

As used herein, to "treat" means reducing the frequency with which symptoms of a disease, disorder, or adverse condition, and the like, are experienced by a patient.

As used herein, the term "pharmaceutically acceptable carrier" means a chemical composition with which the active ingredient may be combined and which, following the combination, can be used to administer the active ingredient to a subject.

The term "lipid" or "lipids" means an organic compound characterized by its preference for non-polar aprotic organic solvents. A lipid may or may not possess an alkyl tail. Lipids according to the present invention include, but are not limited to, the class of compounds known in the art as phospholipids, cholesterols, and dialkyl phosphates.

As used herein, "cholesterol" means the compound and all derivatives and analogs of the compound:

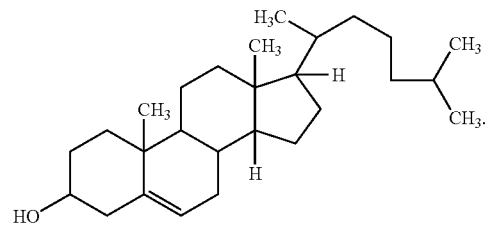 [SMILES: CC(C)CCCC(C)C1CCC2C3CC=C4CC(O)CCC4(C)C3CCC12C]

As used herein, "particle" comprises an agglomeration of multiple units of one or more lipids.

Description

A composition of the present invention is comprised of gelatin and one or more constituents wherein said constituents include liposomes, liposome fragments, and lipid particles.

Traditionally, liposome, liposome fragments, and lipid particles comprised of amphipathic materials have been limited to a lower size distribution of about 40 nanometers. This limit was believed to be a function of the collective sizes of the constituent lipids (phospholipids, cholesterols, dialkylphosphates, etc.) that constituted the membrane structure.

The constituents of a composition of the present invention, however, demonstrate heretofore unobserved sizing and size elasticity. Specifically, constituents of the compositions of the present invention, exist in a dynamic equilibrium in aqueous media wherein the constituents, on average, fluctuate in size from about 6 nanometers to about 60 nanometers in diameter. At any given time, anywhere from about 5% to about 50% of the constituents exhibit an average diameter of about 20 nanometers or less. Due to the nearly constant fluctuations in sizes, the constituents of the compositions of the present invention cannot be physically separated by traditional fractionating means to form discrete populations of differently sized structures. The constituents of a composition of the invention may be, but are not limited to, a liposome, a liposome fragment, and a lipid particle.

The constituents of the composition of the present invention may associate with one or more therapeutic agents or diagnostic agents. Without wishing to be bound by any particular theory, it is believed that constituents having diameters of 20 nanometers or less are sufficiently small to pass through intercellular gaps, thus enabling transport of the associated therapeutic agent or diagnostic agent from the lumen of the gut into the portal blood.

The associated therapeutic agents or diagnostic agents may be bound covalently or noncovalently to one or more constituents of the composition of the present invention. In embodiments of the invention wherein the associated therapeutic or diagnostic agents are bound covalently, the associated therapeutic agent or diagnostic agent may be bound to a chemical group that can be functionalized. Examples of functionalizable groups include, but are not limited to, hydroxy, amino, carboxy, and amido groups. Examples of therapeutic and diagnostic agents that may be covalently bound to a constituent of a composition of the present invention include peptides, various small molecules, nucleic acids, DNA or RNA sequences, and a variety of monoclonal antibodies and glycolipids that act as therapeutic agents, and in addition, other larger proteins.

Alternatively, and more preferably, a constituent of a composition of the invention, may associate with the aforementioned diagnostic or therapeutic agents via non-covalent interactions. Non-covalent interactions enable compatibility of a constituent of the composition of the present invention with a wide variety of diagnostic and therapeutic agents.

Lipids

A constituent of a composition of the present invention comprises one or more lipid components and an optional targeting agent. An embodiment comprising multiple units of a single lipid component is referred to herein as a "lipid particle." An embodiment comprising two or more different lipid components and an optional targeting agent is classified as a liposome or liposome fragment, depending upon the nature of the resulting structure.

Lipid components of the present invention are selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), triethylammonium 2,3-diacetoxypropyl 2-(5-((3aS,6aR)-2-oxohexahydro-1H-thieno[3,4-d]imidazol-4-yl)pentanamido)ethyl phosphate and derivatives thereof. Representative structures are presented in Table 1.

TABLE 1

| Common Name | Chemical Name | Structure |
|---|---|---|
| 1,2-distearoyl-sn-glycero-3-phosphocholine | 2,3-bis(stearoyloxy)propyl 2-(trimethylammonio) ethyl phosphate | 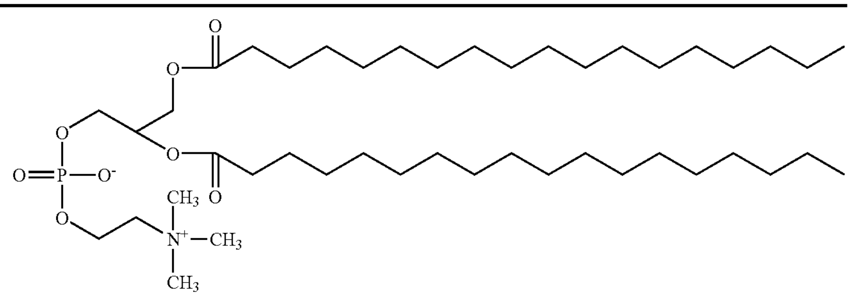 |
| 1,2-dipalmitoyl-sn-glycero-3-phosphocholine | 2,3-bis(palmitoyloxy)propyl 2-(trimethylammonio) ethyl phosphate | 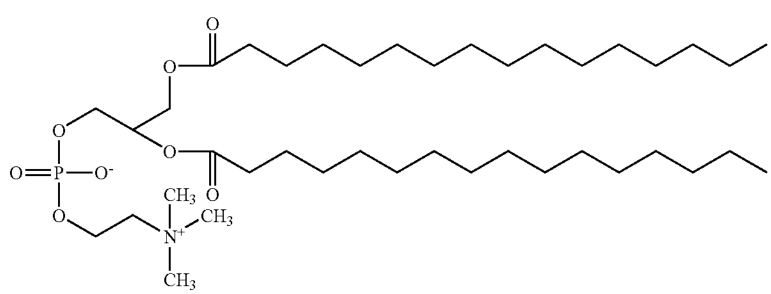 [SMILES: CCCCCCCCCCCCCCCC(=O)OCC(COP(=O)([O-])OCC[N+](C)(C)C)OC(=O)CCCCCCCCCCCCCCC] |
| 1,2-dimyristoyl-sn-glycero-3-phosphocholine | 2,3-bis(tetradecanoyloxy) propyl 2-(trimethylammonio) ethyl phosphate | 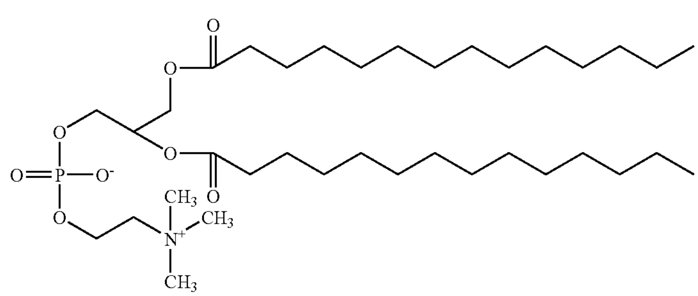 [SMILES: CCCCCCCCCCCCCC(=O)OCC(COP(=O)([O-])OCC[N+](C)(C)C)OC(=O)CCCCCCCCCCCCC] |

TABLE 1-continued

| Common Name | Chemical Name | Structure |
|---|---|---|
| Cholesterol | 10,13-dimethyl-17-(6-methylheptan-2-yl)-2,3,4,7,8,9,10,11,12,13,14,15,16,17-tetradecahydro-1H-cyclopenta[a]-phenanthren-3-ol | 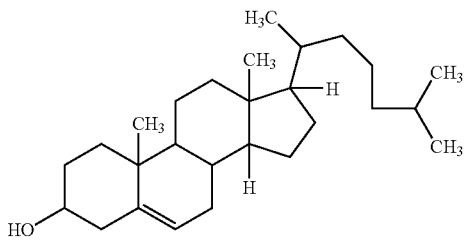 [SMILES: CC(C)CCCC(C)C1CCC2C3CC=C4CC(O)CCC4(C)C3CCC12C] |

By way of non-limiting examples, the constituents of a composition of the present invention may be formed from lipid components mixed in accordance with the following: approximately 61 mole percent 1,2 distearoyl-sn-glycero-3-phosphocholine, approximately 22 mole percent dihexadecyl phosphate, and approximately 16 mole percent cholesterol. In embodiments wherein a constituent incorporates a targeting agent, the above noted mixture may further include from about 1 to about 2 mole percent of at least one targeting agent.

Preparation

Generally, the constituents of a composition of the present invention are formed when at least one lipid component and optional targeting agent are homogenized in an aqueous media via microfluidization or other process involving cavitation.

In an embodiment of the invention, the lipid component(s) and optional targeting agent(s) may be homogenized in 18 mM phosphate buffer at a pH of about 6.0 to a pH of about 8.0. Lipid component concentration in the phosphate buffer may range from about 10 to about 200 mg/ml and any and all whole and partial integers therebetween. In one embodiment, the lipid component concentration is about 30 to about 150 mg/ml. In more preferred embodiment, the lipid component concentration is about 15 to about 50 mg/ml. In a most preferred embodiment, the lipid component concentration is about 28-30 mg/ml.

Homogenization of the aqueous media, lipid component(s), and optional targeting agent may be accomplished via treatment in a device suitable for homogenization. Examples of suitable devices include, but are not limited to, a Polytron® System PT 6100, an M-110-EH microfluidizer, an ultrasonic sonicator, a high pressure membrane filtration apparatus, and a homogenizer extruder.

In instances where a microfluidizer is used, the microfluidizer is preferably operated at a temperature that is greater than the highest transition temperature of a lipid component and most preferably at a temperature greater than about 75° C. Thus, the elevated temperature allows any acyl and alkyl chains present in the lipid component(s) to move fluidly as well as conform to and associate with neighboring hydrocarbon moieties. These non-covalent associations directly result in the formation of a constituent of a composition of the present invention.

Figure 9:
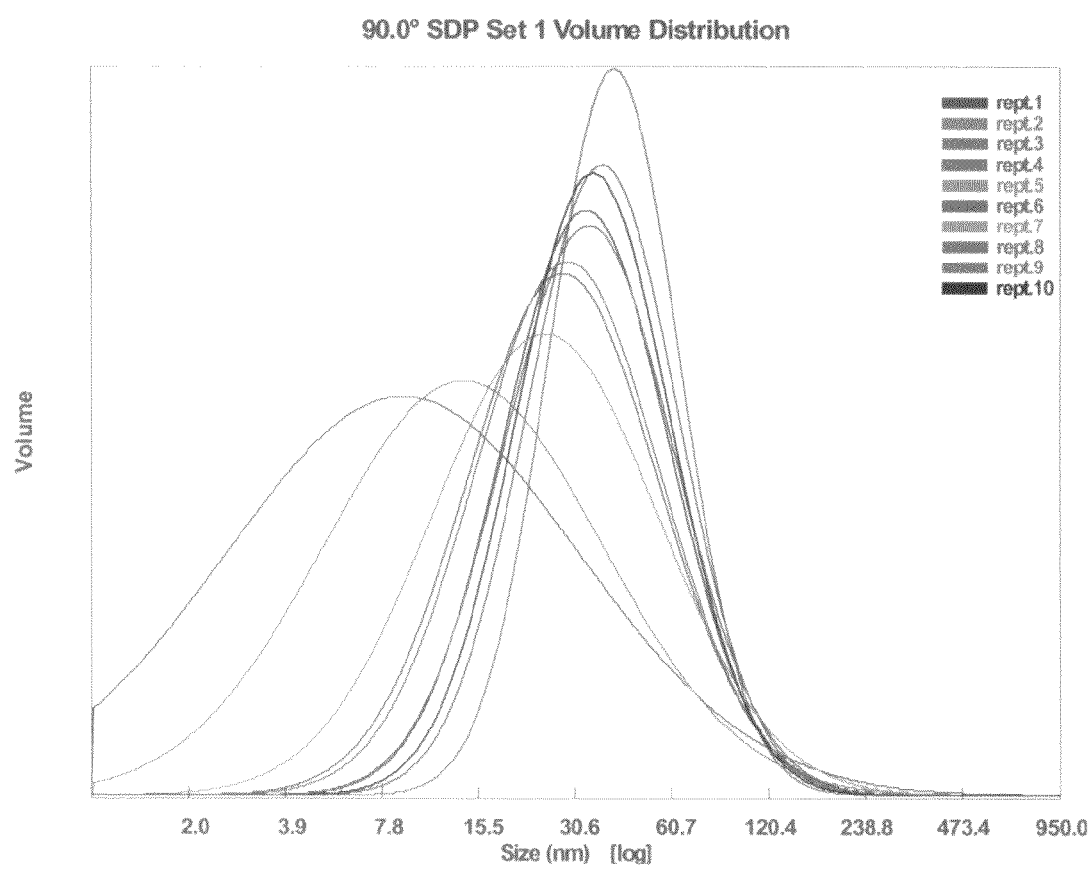
FIG. 9 is a graph of the size distribution of the constituent members of a composition of the invention.

For the microfluidization process, up to about five independent passes are required at 9000 psig in order to achieve dynamic constituent sizing with some constituents possessing radii of less than 20 nanometers. Constituent analysis data generated by a Coulter N-4 Plus Sub-Micron Particle Size Analyzer is shown in FIG. 9 and represents 10 repeated size analyses on the same sample as it remained stationary in the Coulter N-4 Plus Sub-Micron Particle Size Analyzer. This data demonstrates the dynamic nature of constituent sizing and the fluid nature of the interactions between the constituents of the composition of the present invention in aqueous media.

After microfluidization, the resulting constituents may be sterile filtered through a 0.8 micron to 0.2 micron gang Supor™ membrane.

During the process of sub-micron particle formation, hydrogen bonding, ionic bonding, van der Waal's interactions, dipolar interactions, ion-dipole interactions and hydrophobic associations dictate the manner in which the constituents of a composition of the present invention assemble. While not wishing to be bound by any one particular theory, it is believed that the interaction of all of these forces, to varying extents, under the conditions noted above, lead to the dynamically sized constituents of the present invention.

Incorporation of a Targeting Agent

In certain embodiments, a constituent of the present invention may optionally comprise a targeting agent. Targeting agents alter a constituent's bio-distribution and further enhance the efficacy of an associated therapeutic agent. For example, a constituent of a composition of the present invention may incorporate one or more targeting agents that act to target the constituent to a specific cellular or extracellular receptor. Alternatively, by way of a non-limiting example, the targeting agent may mask the constituent from reticuloendothelial (microphage) recognition.

In one embodiment, a targeting agent facilitates delivery of insulin to the liver to control post-prandial glycogen storage and encompasses a class of molecules referred to as "hepatocyte target molecule" (HTM). HTM examples include biotin derived targeting agents such as 1,2-dipalmitoyl-sn-glycero-3-phosphoethanolamine-N-(biotinyl) and metal derived targeting agents such as poly[Cr-bis(N-2,6-diisopropylphenylcarbamoylmethyl iminodiacetic acid)]. Metal-derived targeting agents and biotin derived targeting agents are discussed below and are fully described in U.S. Pat. Nos. 7,169,410 and 4,603,044; PCT application PCT/US06/19119; and U.S. patent application Ser. Nos. 11/384,728, and 11/384,659. Additional examples of biotin-derived targeting agents are disclosed in Table 5.

When the targeting agent comprises biotin, iminobiotin, carboxybiotin, biocytin, or iminobiocytin, the biotin, iminobiotin, carboxybiotin, biocytin, or iminobiocytin molecules may be bound via an amide bond to the nitrogen of a phospholipid molecule such as 1,2-dipalmitoyl-sn-glycero-3-phosphoethanolamine. The compounds may likewise be bound to a molecule such as cholesterol through an ester linkage. In the case of biocytin and iminobiocytin, the compounds may be bound to benzoyl thioacetyl triglycine via an amide bond between the terminal nitrogen of iminiobiocytin and the terminal carbonyl of benzoyl thioacetyl triglycine. Alternative bond connectivities to those described above are possible and considered to be within thescope of the present invention.

TABLE 5

| | | |
|---|---|---|
| 1 | N-hydroxysuccinimide (NHS) biotin<br>2,5-dioxopyrrolidin-1-yl 5-((3aS,6aR)-2-oxohexahydro-1H-thieno[3,4-d]imidazol-4-yl) pentanoate | 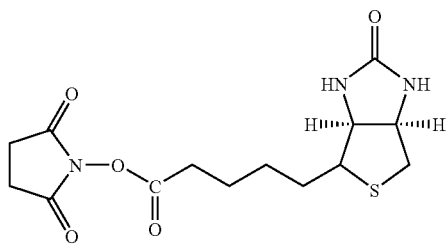 [SMILES: O=C1N[C@H]2CSC(CCCCC(=O)ON3C(=O)CCC3=O)[C@H]2N1] |
| 2 | sulfo-NHS-biotin<br>sodium 2,5-dioxo-3-(trioxidanylthio)pyrrolidin-1-yl 5-((3aS,6aR)-2-oxohexahydro-1H-thieno[3,4-d]imidazol-4-yl) pentanoate | 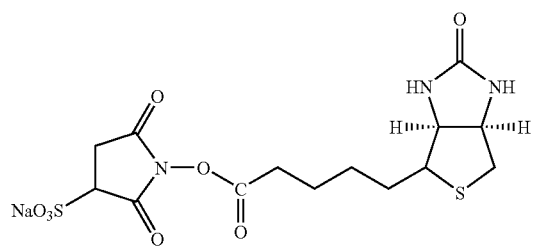 |
| 3 | N-hydroxysuccinimide long chain biotin<br>2,5-dioxopyrrolidin-1-yl 6-(5-((3aS,6aR)-2-oxohexahydro-1H-thieno[3,4-d]imidazol-4-yl) pentanamido)hexanoate | 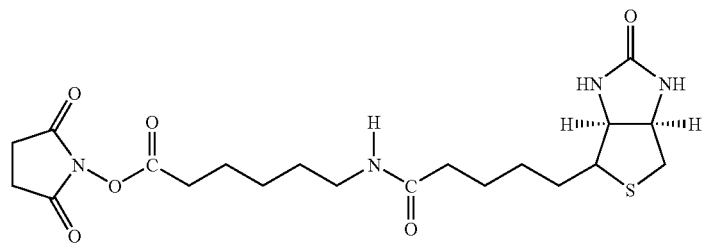 [SMILES: O=C(CCCCC1SC[C@@H]2NC(=O)N[C@H]12)NCCCCCC(=O)ON1C(=O)CCC1=O] |
| 4 | sulfo-N-hydroxysuccinimide long chain biotin<br>sodium 2,5-dioxo-3-(trioxidanylthio) pyrrolidin-1-yl 6-(5-((3aS,6aR)-2-oxohexahydro-1H-thieno[3,4-d] imidazol-4-yl)pentanamido) hexanoate | 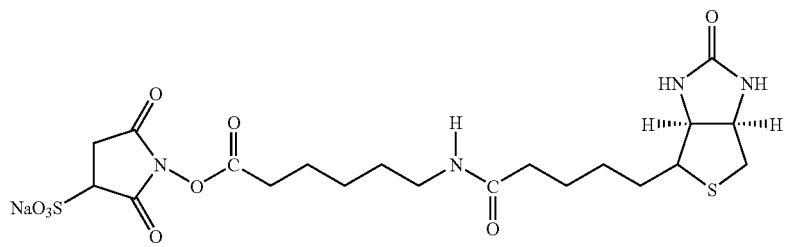 |
| 5 | D-biotin<br>5-((3aS,6aR)-2-oxohexahydro-1H-thieno[3,4-d]imidazol-4-yl) pentanoic acid | 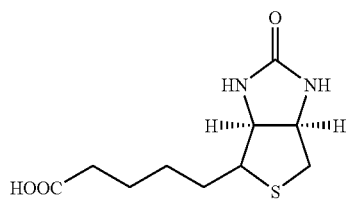 [SMILES: O=C(O)CCCCC1SC[C@@H]2NC(=O)N[C@H]12] |
| 6 | Biocytin<br>2-amino-6-(5-((3aS,6aR)-2-oxohexahydro-1H-thieno[3,4-d]-imidazol-4-yl) pentanamido) hexanoic acid | 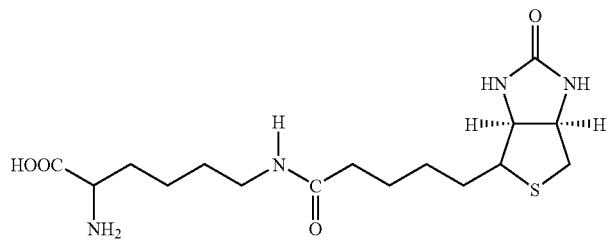 [SMILES: NC(CCCCNC(=O)CCCCC1SC[C@@H]2NC(=O)N[C@H]12)C(=O)O] |

TABLE 5-continued

| 7 | sulfo-N-hydroxysuccinimide-S-S-biotin
sodium 2,5-dioxo-3-(trioxidanylthio) pyrrolidin-1-yl 3-((2-(4-((3aS,6aR)-2-oxohexahydro-1H-thieno[3,4-d]imidazol-4-yl)butylamino)ethyl)disulfanyl)propanoate | 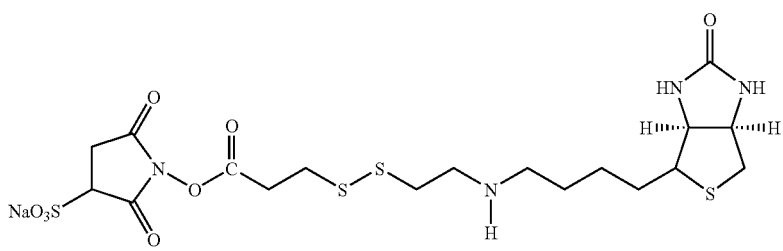 |

| 8 | biotin-BMCC
4-((2,5-dioxo-2,5-dihydro-1H-pyrrol-1-yl)methyl)-N-(4-(5-((3aS,6aR)-2-oxohexahydro-1H-thieno[3,4-d]imidazol-4-yl)pentanamido)butyl)cyclohexanecarboxamide | 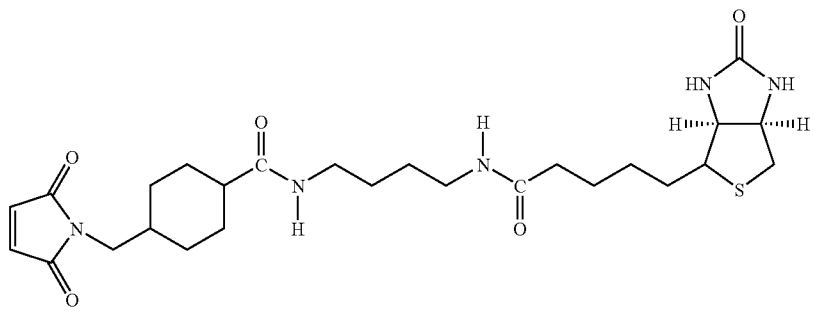 [SMILES: O=C(CCCCC1SC[C@@H]2NC(=O)N[C@H]12)NCCCCNC(=O)C1CCC(CN2C(=O)C=CC2=O)CC1] |

| 9 | biotin-HPDP
5-((3aS,6aR)-2-oxohexahydro-1H-thieno[2,4-d]imidazol-4-yl)-N-(6-(3-pyridin-2-yldisulfanyl)propanamido)hexyl)pentanamide | 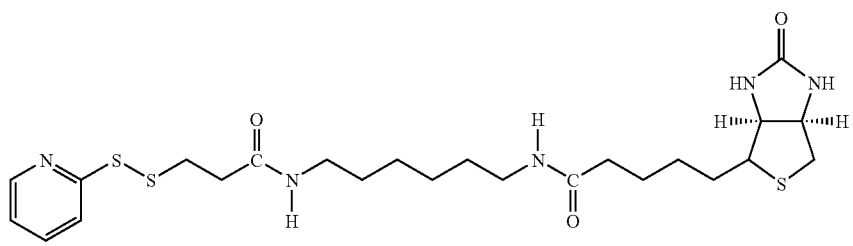 [SMILES: O=C(CCCCC1SC[C@@H]2NC(=O)N[C@H]12)NCCCCCCNC(=O)CCSSc1ccccn1] |

| 10 | iodoacetyl-LC-biotin
N-(6-(2-iodoacetamido)hexyl)-5-((3aS,6aR)-2-oxohexahydro-1H-thieno[3,4-d]-imidazol-4-yl)pentanamide | 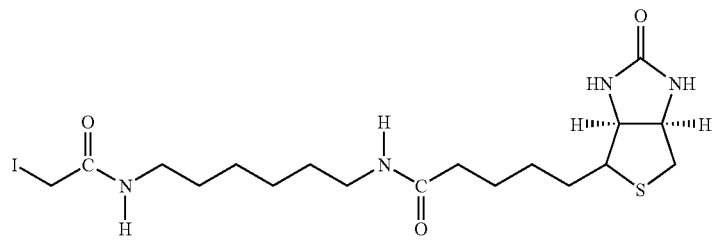 [SMILES: O=C(CI)NCCCCCCNC(=O)CCCCC1SC[C@@H]2NC(=O)N[C@H]12] |

| 11 | biotin-hydrazide
5-((3aS,6aR)-2-oxohexahydro-1H-thieno[3,4-d]imidazol-4-yl)pentanehydrazide | 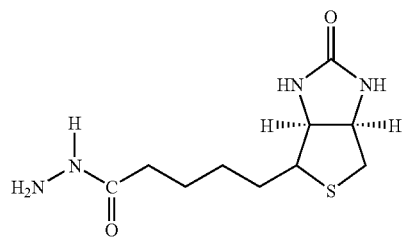 [SMILES: NNC(=O)CCCCC1SC[C@@H]2NC(=O)N[C@H]12] |

| 12 | biotin-LC-hydrazide
N-(6-hydrazinyl-6-oxohexyl)-5-((3aS,6aR)-2-oxohexahydro-1H-thieno[3,4-d]imidazol-4-yl)pentanamide | 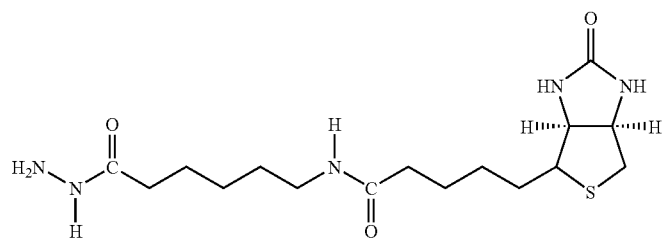 [SMILES: NNC(=O)CCCCCNC(=O)CCCCC1SC[C@@H]2NC(=O)N[C@H]12] |

TABLE 5-continued

| 13 | biocytin hydrazide<br>N-(5-amino-6-hydrazinyl-6-oxohexyl)-5-((3aS,6aR)-2-oxohexahydro-1H-thieno[3,4-d]-imidazol-4-yl)pentanamide | 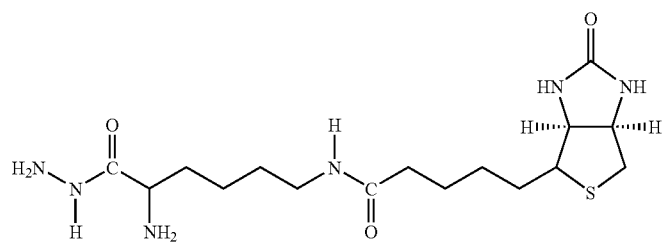 [SMILES: NNC(=O)C(N)CCCCNC(=O)CCCCC1SC[C@@H]2NC(=O)N[C@H]12] |
| --- | --- | --- |
| 14 | biotin cadaverine<br>N-(5-aminopentyl)-5-((3aS,6aR)-2-oxohexahydro-1H-thieno[3,4-d]imidazol-4-yl)pentanamide | 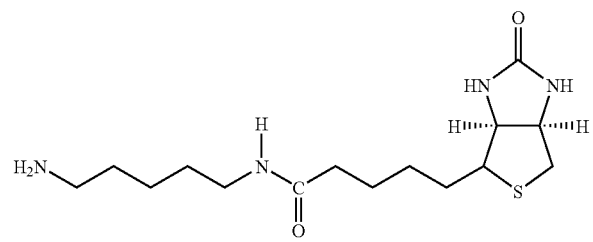 [SMILES: NCCCCCNC(=O)CCCCC1SC[C@@H]2NC(=O)N[C@H]12] |
| 15 | Carboxybiotin<br>(3aS,6aR)-4-(4-carboxybutyl)-2-oxohexahydro-1H-thieno[3,4-d]-imidazole-1-carboxylic acid | 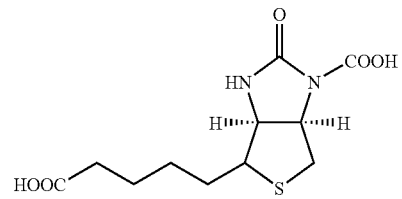 [SMILES: O=C(O)CCCCC1SC[C@H]2[C@@H]1NC(=O)N2C(=O)O] |
| 16 | Photobiotin<br>N-(3((3-(4-azido-2-nitrophenylamino)propyl)(methyl)amino)propyl)-5-((3aS,6aR)-2-oxohexahydro-1H-thieno[3,4-d]-imidazol-4-yl)pentanamide | 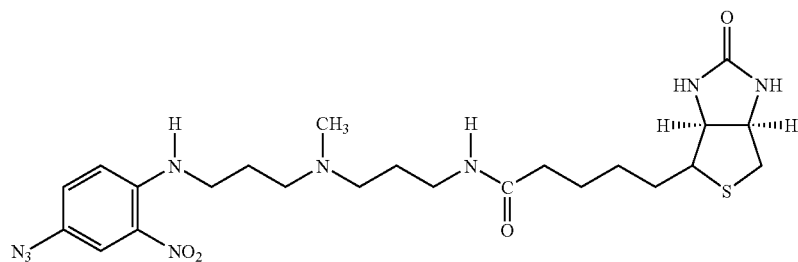 [SMILES: CN(CCCNC(=O)CCCCC1SC[C@@H]2NC(=O)N[C@H]12)CCCNc1ccc(N=[N+]=[N-])cc1[N+](=O)[O-]] |
| 17 | ρ-aminobenzoyl biocytin trifluoroacetate<br>2-(4-aminobenzamido)-6-(5-((3aS,6aR)-2-oxohexahydro-1H-thieno[3,4-d]imidazol-4-yl)pentanamido)hexanoic acid 2,2,2-trifluoroacetate | 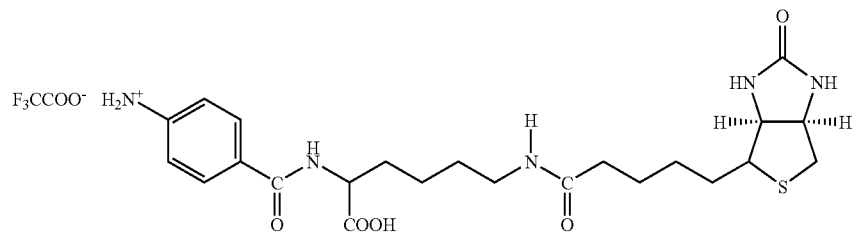 [SMILES: "F3CCOO-" ; [NH3+]c1ccc(C(=O)NC(CCCCNC(=O)CCCCC2SC[C@@H]3NC(=O)N[C@H]23)C(=O)O)cc1] |
| 18 | ρ-diazobenzoyl biocytin<br>4-(1-carboxy-5-(5-((3aS,6aR)-2-oxohexahydro-1H-thieno[3,4-d]-imidazol-4-yl)pentanamido)pentylcarbamoyl)benzenediazonium chloride | 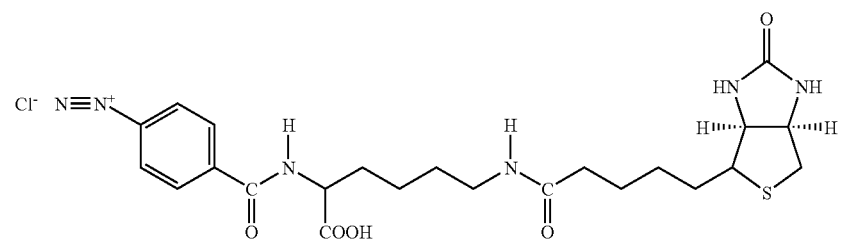 [SMILES: [Cl-] ; N#[N+]c1ccc(C(=O)NC(CCCCNC(=O)CCCCC2SC[C@@H]3NC(=O)N[C@H]23)C(=O)O)cc1] |

TABLE 5-continued

| | | |
|---|---|---|
| 19 | biotin DHPE<br>G⁺ = Li⁺, Na⁺, K⁺, (Et₃NH)⁺<br>2,3-diacetoxypropyl 2-(5-((3aS,6aR)-2-oxohexahydro-1H-thieno[3,4-d]imidazol-4-yl)pentanamido)ethyl phosphate | 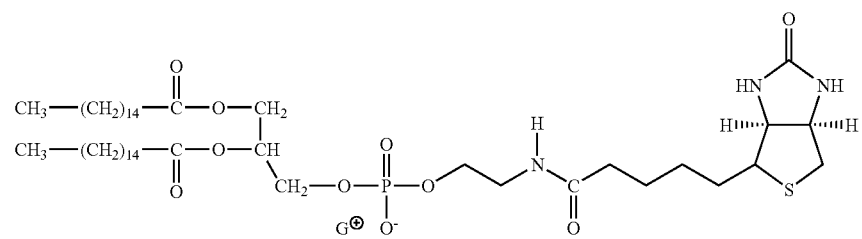 |
| 20 | biotin-X-DHPE<br>G⁺ = Li⁺, Na⁺, K⁺, (Et₃NH)⁺<br>2,3-diacetoxypropyl 2-(6-(5-((3aS,6aR)-2-oxohexahydro-1H-thieno[3,4-d]imidazol-4-yl)pentanamido)hexanamido)ethyl phosphate | 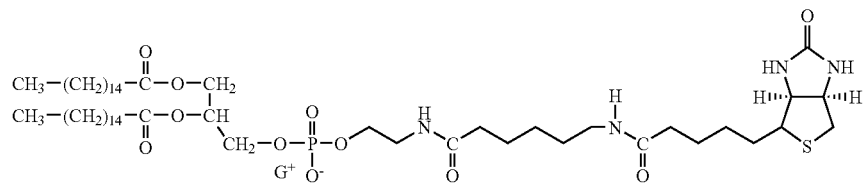 |
| 21 | 12-((biotinyl)amino)dodecanoic acid<br>12-(5-((3aS,6aR)-2-oxohexahydro-1H-thieno[3,4-d]imidazol-4-yl) pentanamido) dodecanoic acid | 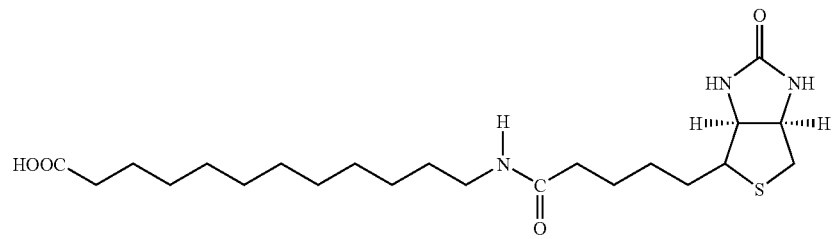 [SMILES: O=C(O)CCCCCCCCCCCNC(=O)CCCCC1SC[C@@H]2NC(=O)N[C@H]12] |
| 22 | 12-((biotinyl)amino)dodecanoic acid succinimidyl ester<br>2,5-dioxopyrrolidin-1-yl 12-(5-((3aS,6aR)-2-oxohexahydro-1H-thieno[3,4-d]imidazol-4-yl)pentanamido)dodecanoate | 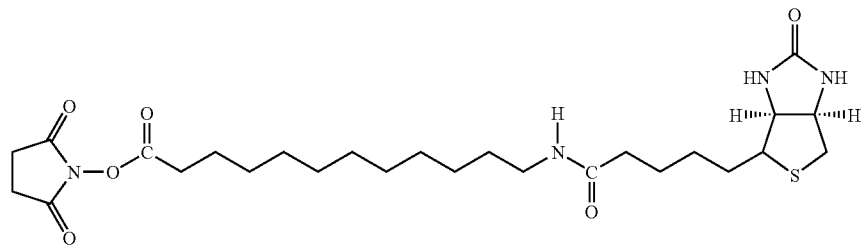 [SMILES: O=C(CCCCC1SC[C@@H]2NC(=O)N[C@H]12)NCCCCCCCCCCCC(=O)ON1C(=O)CCC1=O] |
| 23 | S-biotinyl homocysteine<br>4-mercapto-2-(5-((3aS,6aR)-2-oxohexahydro-1H-thieno[3,4-d]-imidazol-4-yl) pentanamido) butanoic acid | 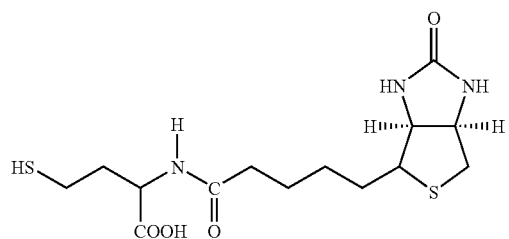 [SMILES: O=C(CCCCC1SC[C@@H]2NC(=O)N[C@H]12)NC(CCS)C(=O)O] |
| 24 | biocytin-X<br>2-amino-6-(6-(5-((3aS,6aR)-2-oxohexahydro-1H-thieno[3,4-d]-imidazol-4-yl)pentanamido)hexanamido)hexanoic acid | 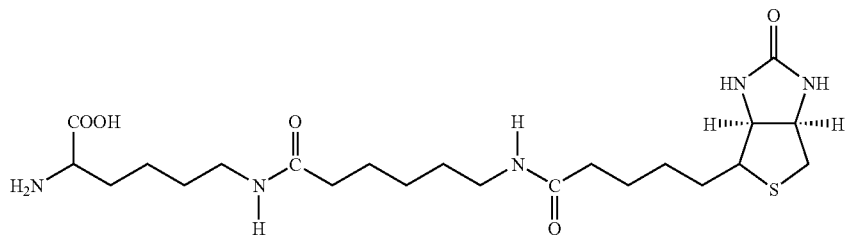 [SMILES: NC(CCCCNC(=O)CCCCCNC(=O)CCCCC1SC[C@@H]2NC(=O)N[C@H]12)C(=O)O] |

TABLE 5-continued

| | | |
|---|---|---|
| 25 | biocytin x-hydrazide<br>N-(5-amino-6-hydrazinyl-6-oxohexyl)-6-(5-((3aS,6aR)-2-oxohexahydro-1H-thieno[3,4-d]imidazol-4-yl)pentanamido)hexanamide | 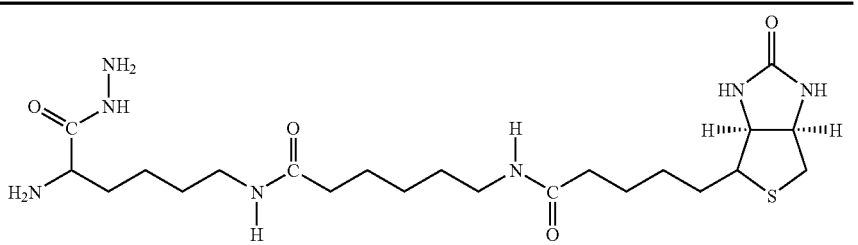 |
| 26 | Biotinethylenediamine<br>N-(2-aminomethyl)-5-((3aS,6aR)-2-oxohexahydro-1H-thieno[3,4-d]imidazol-4-yl)pentanamide | 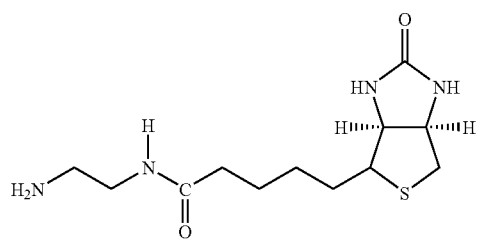 [SMILES: NCCNC(=O)CCCCC1SC[C@@H]2NC(=O)N[C@H]12] |
| 27 | biotin-X<br>6-(5-((3aS,6aR)-2-oxohexahydro-1H-thieno[3,4-d]imidazol-4-yl)pentanamido)hexanoic acid | 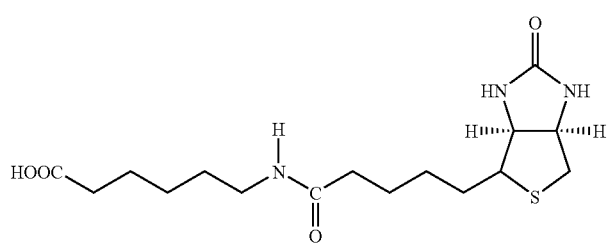 [SMILES: O=C(O)CCCCCNC(=O)CCCCC1SC[C@@H]2NC(=O)N[C@H]12] |
| 28 | biotin-X-ethylenediamine<br>N-(2-aminoethyl)-6-(5-((3aS,6aR)-2-oxohexahydro-1H-thieno[3,4-d]imidazol-4-yl)pentanamido)hexanamide | 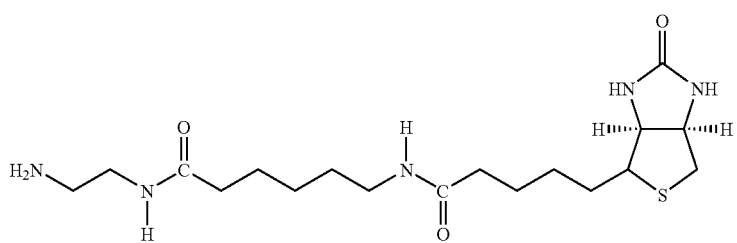 [SMILES: NCCNC(=O)CCCCCNC(=O)CCCCC1SC[C@@H]2NC(=O)N[C@H]12] |
| 29 | biotin-XX hydrazide<br>N-(6-hydrazinyl-6-oxohexyl)-6-(5-((3aS,6aR)-2-oxohexahydro-1H-thieno[3,4-d]imidazol-4-yl)pentanamido)hexanamide | 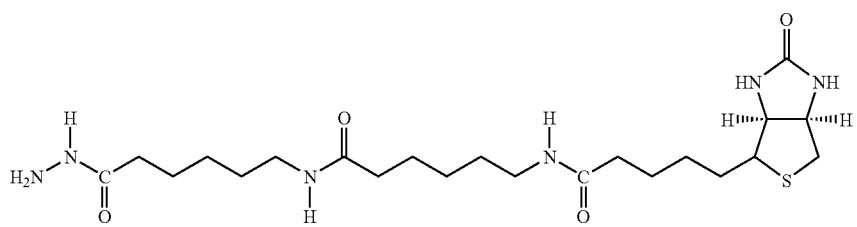 [SMILES: NNC(=O)CCCCCNC(=O)CCCCCNC(=O)CCCCC1SC[C@@H]2NC(=O)N[C@H]12] |
| 30 | biotin-XX-SE<br>2,5-dioxopyrrolidin-1-yl 6-(6-(5-((3aS,6aR)-2-oxohexahydro-1H-thieno[3,4-d]imidazol-4-yl)pentanamido)hexanamido)hexanoate | 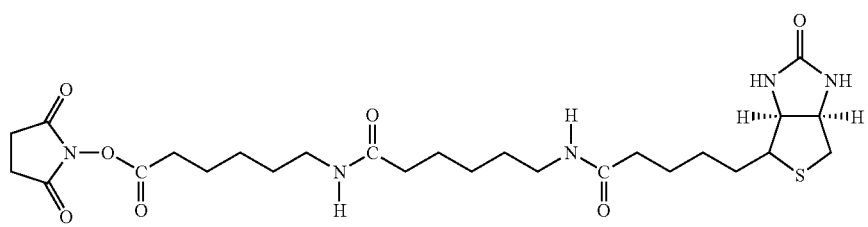 [SMILES: O=C(CCCCCNC(=O)CCCCC1SC[C@@H]2NC(=O)N[C@H]12)NCCCCCC(=O)ON1C(=O)CCC1=O] |
| 31 | biotin-XX,SSE<br>sodium 2,5-dioxo-1-(6-(6-(5-((3aS,6aR)-2-oxohexahydro-1H-thieno[3,4-d]imidazol-4-yl)pentanamido)hexanamido)hexanoyloxy)pyrrolidine-3-sulfonate | 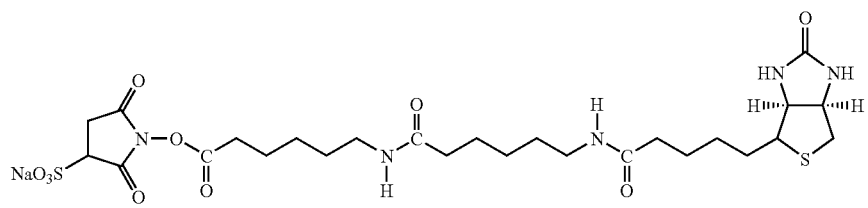 |

TABLE 5-continued

| | | |
|---|---|---|
| 32 | biotin-X-cadaverine<br>5-(6-(5-((3aS,6aR)-2-oxohexahydro-1H-thieno[3,4-d]imidazol-4-yl)pentanamido)hexanamido)pentan-1-aminium 2,2,2-trifluoroacetate | 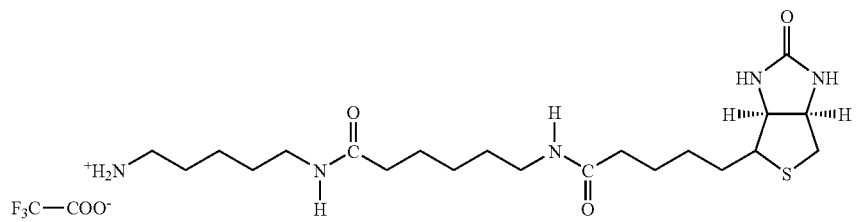 |
| 33 | α-(t-BOC)biocytin<br>2-(tert-butoxycarbonylamino)-6-(5-((3aS,6aR)-2-oxohexahydro-1H-thieno[3,4-d]imidazol-4-yl)pentanamido)hexanoic acid | 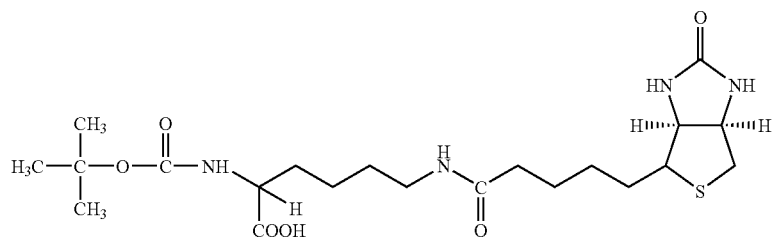 [SMILES: CC(C)(C)OC(=O)NC(CCCCNC(=O)CCCCC1SC[C@@H]2NC(=O)N[C@H]12)C(=O)O] |
| 34 | N-(biotinyl)-N'-(iodoacetyl)ethylenediamine<br>N-(2-(2-iodoacetamido)ethyl)-5-((3aS,6aR)-2-oxohexahydro-1H-thieno[3,4-d]imidazol-4-yl)pentanamide | 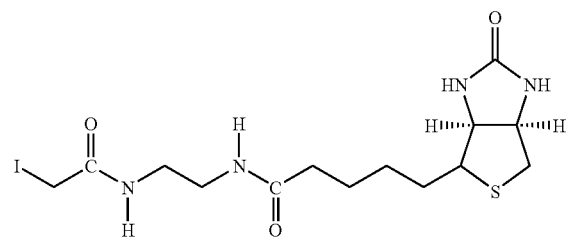 [SMILES: O=C(CI)NCCNC(=O)CCCCC1SC[C@@H]2NC(=O)N[C@H]12] |
| 35 | DNP-X-biocytin-X-SE<br>2,5-dioxopyrrolidin-1-yl 2-(6-(6-(2,4-dinitrophenylamino)hexanamido)hexanamido)-6-(5-((3aS,6aR)-2-oxohexahydro-1H-thieno[3,4-d]imidazol-4-yl)pentanamido)hexanamido)hexanoate | 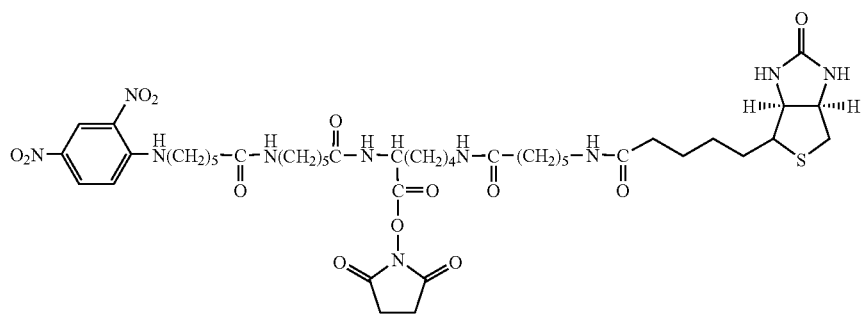 |
| 36 | biotin-X-hydrazide<br>N-(6-hydrazinyl-6-oxohexyl)-5-((3aS,6aR)-2-oxohexahydro-1H-thieno[3,4-d]imidazol-4-yl)pentanamide | 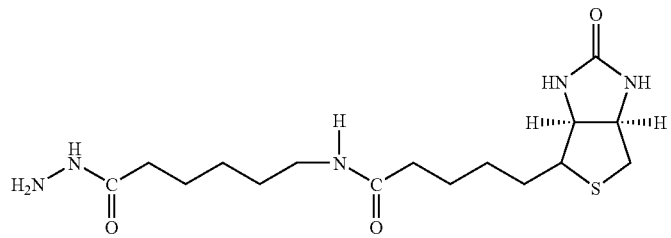 [SMILES: NNC(=O)CCCCCNC(=O)CCCCC1SC[C@@H]2NC(=O)N[C@H]12] |
| 37 | norbiotinamine hydrochloride<br>4-((3aS,6aR)-2-oxohexahydro-1H-thieno[3,4-d]imidazol-4-yl)butan-1-aminium chloride | 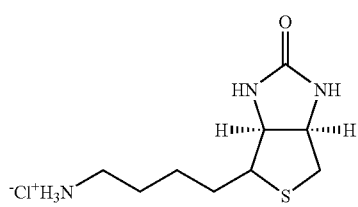 |

TABLE 5-continued

| | | |
|---|---|---|
| 38 | 3-(N-maleimidylpropionyl) biocytin<br>2-(3-(2,5-dioxo-2,5-dihydro-1H-pyrrol-1-yl)propanamido)-6-(5-((3aS,6aR)-2-oxohexahydro-1H-thieno[3,4-d]imidazol-4-yl)pentanamido)hexanoic acid | 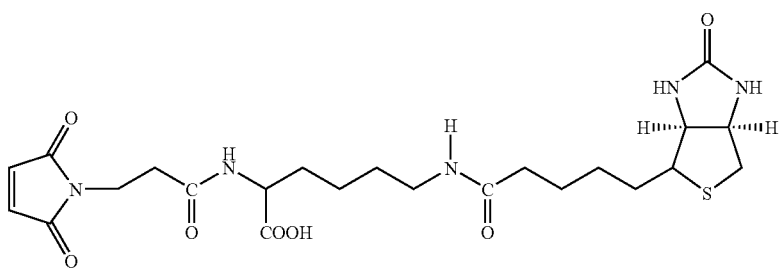 [SMILES: O=C(CCCCC1SC[C@@H]2NC(=O)N[C@H]12)NCCCCC(NC(=O)CCN1C(=O)C=CC1=O)C(=O)O] |
| 39 | ARP;<br>N'-(2-(aminooxy)acetyl)-5-((3aS,6aR)-2-oxohexahydro-1H-thieno[3,4-d]imidazol-4-yl)pentanehydrazide | 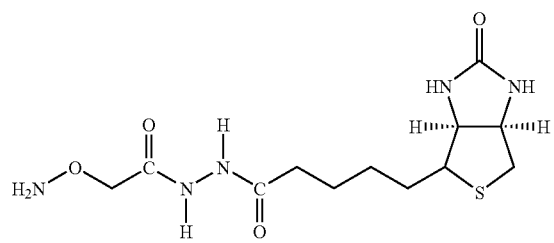 [SMILES: NOCC(=O)NNC(=O)CCCCC1SC[C@@H]2NC(=O)N[C@H]12] |
| 40 | biotin-1-sulfoxide<br>5-((3aS,6aR)-2-oxohexahydro-1H-thieno[3,4-d]imidazol-4-yl)pentanoic acid sulfoxide | 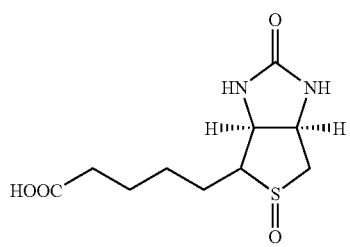 [SMILES: O=C(O)CCCCC1[C@H]2NC(=O)N[C@H]2CS1=O] |
| 41 | biotin methyl ester<br>methyl 5-((3aS,6aR)-2-oxohexahydro-1H-thieno[3,4-d]imidazol-4-yl)pentanoate | 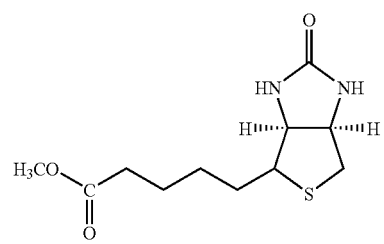 [SMILES: COC(=O)CCCCC1SC[C@@H]2NC(=O)N[C@H]12] |
| 42 | biotin-maleimide<br>6-(2,5-dioxo-2,5-dihydro-1H-pyrrol-1-yl)-N'-(5-((3aS,6aR)-2-oxohexahydro-1H-thieno[3,4-d]imidazol-4-yl)pentanoyl)hexanehydrazide | 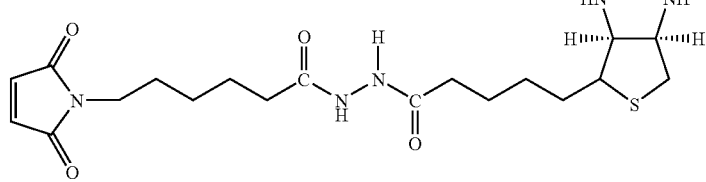 |
| 43 | Biotin-poly(ethyleneglycol) amine<br>aminomethyl polyethylene 5-((3aS,6aR)-2-oxohexahydro-1H-thieno[3,4-d]imidazol-4-yl)pentanoate | 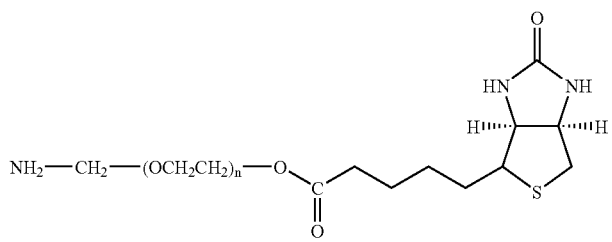 |

TABLE 5-continued

| 44 | (+) biotin 4-amidobenzoic acid sodium salt<br>sodium 4-(5-((3aS,6aR)-2-oxohexahydro-1H-thieno[3,4-d]imidazol-4-yl)pentanamido) benzoate | 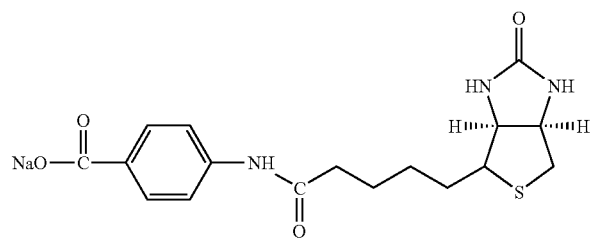 |
| --- | --- | --- |
| 45 | Biotin 2-N-acetylamino-2-deoxy-β-D-glucopyranoside ((2R,5S)-3-acetamido-4,5-dihydroxy-6-(hydroxymethyl)-2,3,4,5,6-pentamethyltetrahydro-2H-pyran-2-yl)methyl 5-((3aS,6aR)-2-oxohexahydro-1H-thieno[3,4-d]imidazol-4-yl) pentanoate | 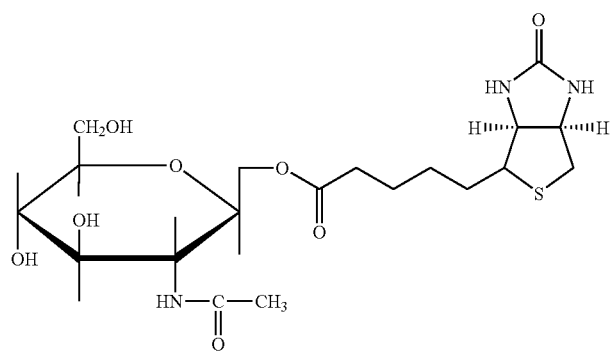 |
| 46 | Biotin-α-D-N-acetylneuraminide (2S,5R)-5-acetamido-4-hydroxy-3,3,4,5,6-pentamethyl-2-((5-((3aS,6aR)-2-oxohexahydro-1H-thieno[3,4-d]imidazol-4-yl)pentanoyloxy)methyl)-6-(1,2,3-trihydroxypropyl) tetrahydro-2H-pyran-2-carboxylic acid | 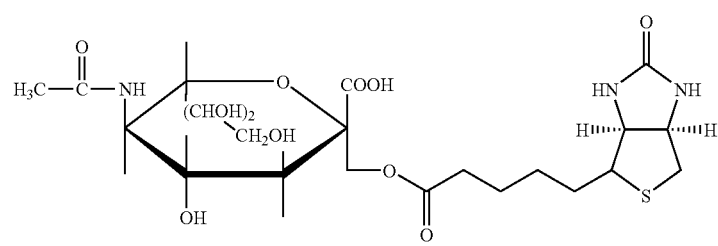 |
| 47 | Biotin-α-L-fucoside ((2R,5S)-3,4,5-trihydroxy-2,3,4,5,6,6-hexamethyltetrahydro-2H-pyran-2-yl)methyl 5-((3aS,6aR)-2-oxohexahydro-1H-thieno[3,4-d]-imidazol-4-yl)pentanoate | 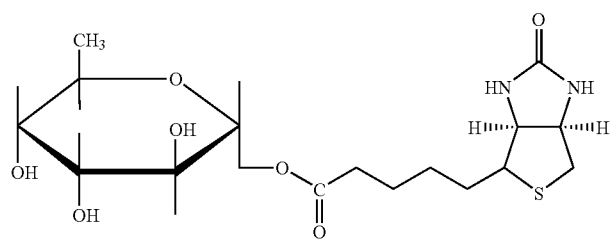 |
| 48 | Biotin lacto-N-bioside<br>See end of table for name | 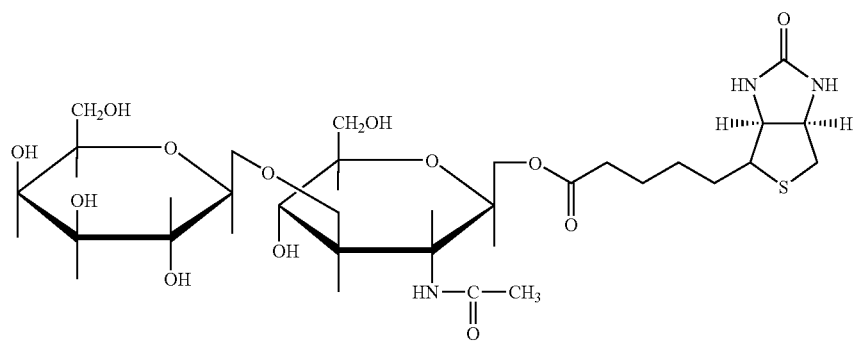 |

TABLE 5-continued

| | | |
|---|---|---|
| 49 | Biotin-Lewis-A trisaccharide<br>See end of table for name | 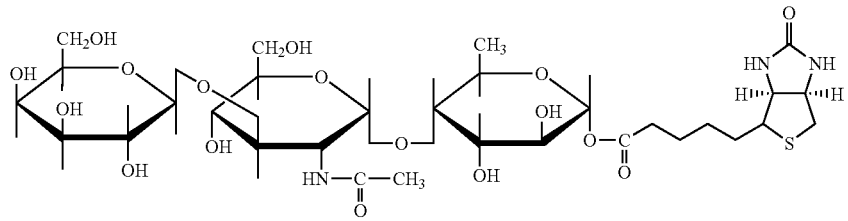 |
| 50 | Biotin-Lewis-Y tetrasaccharide<br>See end of table for name | 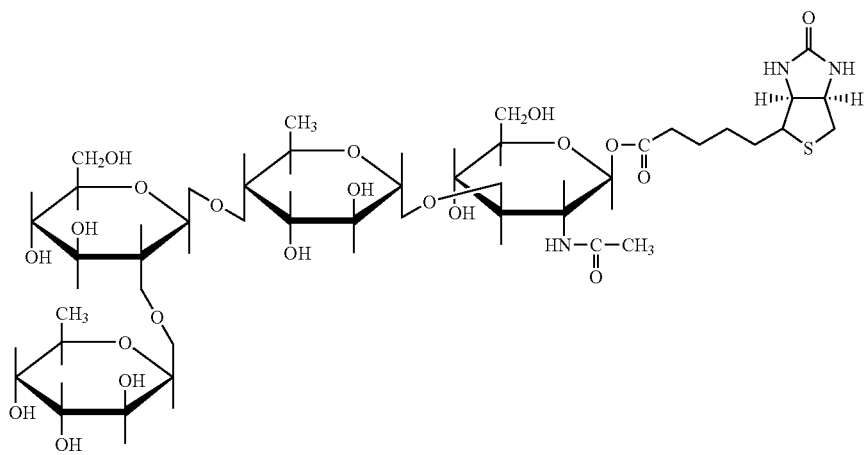 |
| 51 | Biotin-α-D-mannopyranoside<br>((1R,4R)-2,3,4-trihydroxy-5-<br>(hydroxymethyl)-1,2,3,4,5-<br>pentamethylcyclohexyl)methyl<br>5-((3aS,6aR)-2-oxohexahydro-<br>1H-thieno[3,4-d]imidazol-4-yl)<br>pentanoate | 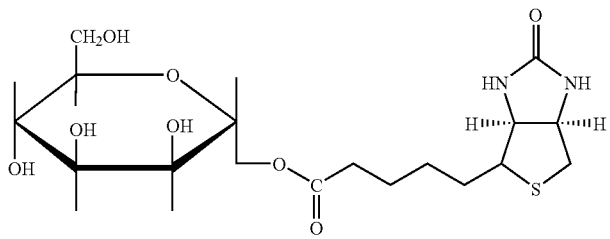 |
| 52 | biotin 6-O-phospho-α-D-<br>mannopyranoside<br>((2R,5S)-3,4,5-trihydroxy-<br>2,3,4,5-pentamethyl-6-<br>(phosphonooxymethyl)tetrahydro-<br>2H-pyran-2-yl)methyl 5-<br>((3aS,6aR)-2-oxohexahydro-1H-<br>thieno[3,4-d]imidazol-4-yl)<br>pentanoate | 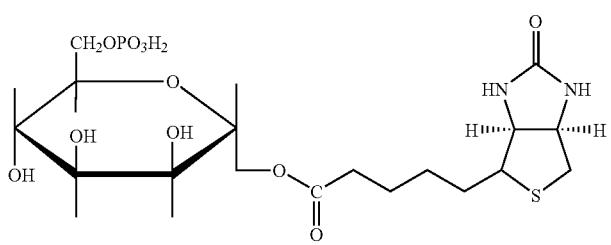 |

Names of Compounds 48-50:

48. ((2R,5S)-3-acetamido-5-hydroxy-6-(hydroxymethyl)-2,3,4,6-tetramethyl-4-((((2S,5R)-3,4,5-trihydroxy-6-(hydroxymethyl)-2,3,4,5,6-pentamethyltetrahydro-2H-pyran-2-yl)methoxy)methyl)tetrahydro-2H-pyran-2-yl)methyl 5-((3aS,6aR)-2-oxohexahydro-1H-thieno[3,4-d]imidazol-4-yl)pentanoate((2R,5S)-3-acetamido-5-hydroxy-6-(hydroxymethyl)-2,3,4,6-tetramethyl-4-((((2S,5R)-3,4,5-trihydroxy-6-(hydroxymethyl)-2,3,4,5,6-pentamethyltetrahydro-2H-pyran-2-yl)methoxy)methyl)tetrahydro-2H-pyran-2-yl)methyl 5-((3aS,6aR)-2-oxohexahydro-1H-thieno[3,4-d]imidazol-4-yl)pentanoate 49. (2R,3R,5S)-5-((((2S,3S,5S)-3-acetamido-5-hydroxy-6-(hydroxymethyl)-2,4,6-trimethyl-4-((((2S,5R)-3,4,5-trihydroxy-6-(hydroxymethyl)-2,3,4,5,6-pentamethyltetrahydro-2H-pyran-2-yl)methoxy)methyl)tetrahydro-2H-pyran-2-yl)methoxy)methyl)-3,4-dihydroxy-2,4,5,6,6-pentamethyltetrahydro-2H-pyran-2-yl 5-((3aS,6aR)-2-oxohexahydro-1H-thieno[3,4-d]imidazol-4-yl)pentanoate 50. (2S,5S)-3-acetamido-4-((((2R,5S)-5-((((2R,5S)-4,5-dihydroxy-6-(hydroxymethyl)-2,3,4,5,6-pentamethyl-3-((((2S,5S)-3,4,5-trihydroxy-2,3,4,5,6,6-hexamethyltetrahydro-2H-pyran-2-yl)methoxy)methyl)tetrahydro-2H-pyran-2-yl)methoxy)methyl)-3,4-dihydroxy-2,3,4,5,6,6-hexamethyltetrahydro-2H-pyran-2-yl)methoxy)methyl)-5-hydroxy-6-(hydroxymethyl)-2,3,4,5,6-pentamethyltetrahydro-2H-pyran-2-yl 5-((3aS,6aR)-2-oxohexahydro-1H-thieno[3,4-d]imidazol-4-yl)pentanoate Structures of iminobiotin compounds are not shown in Table 2. However, the iminobiotin structures are analogs of the biotin structure where the biotin group is replaced by an iminobiotin group. An example is shown below.

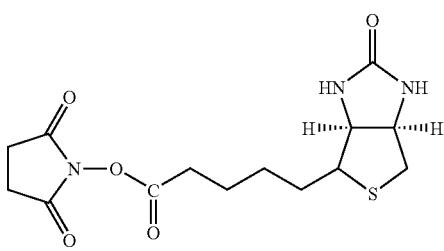

N-hydroxysuccinimide biotin

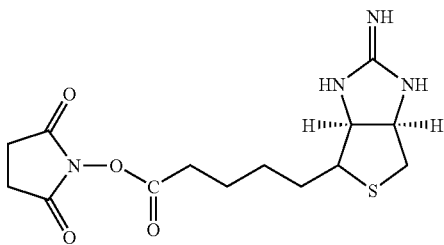

N-hydroxysuccinimide iminobiotin

In an embodiment of the invention, metal derived targeting agents may be polymeric or monomeric. Polymeric metal derive targeting agents are fully described in U.S. Pat. No. 7,169,410. Monomeric metal derived targeting agents are described in U.S. Pat. No. 4,603,044. Whether polymeric or monomeric, the compounds generally comprise a metal (typically purchased as an inorganic salt) that may be selected from the transition and inner transition metals or neighbors of the transition metals. The transition and inner transition metals from which the metal is selected include: Sc (scandium), Y (yttrium), La (lanthanum), Ac (actinium), the actinide series; Ti (titanium), Zr (zirconium), Hf (hafnium), V (vanadium), Nb (niobium), Ta (tantalum), Cr (chromium), Mo (molybdenum), W (tungsten), Mn (manganese), Tc (technetium), Re (rhenium), Fe (iron), Co (cobalt), Ni (nickel), Ru (ruthenium), Rh (rhodium), Pd (palladium), Os (osmium), Ir (iridium), and Pt (platinum). The neighbors of the transition metals from which the metal may be selected are: Cu (copper), Ag (silver), Au (gold), Zn (zinc), Cd (cadmium), Hg (mercury), Al (aluminum), Ga (gallium), In (indium), Tl (thallium), Ge (germanium), (tin), Pb (lead), Sb (antimony) and Bi (bismuth), and Po (polonium). Preferably, the metal is chromium.

Non-limiting examples of useful salts include chromium chloride (III) hexahydrate; chromium (III) fluoride tetrahydrate; chromium (III) bromide hexahydrate; zirconium (IV) citrate ammonium complex; zirconium (IV) chloride; zirconium (IV) fluoride hydrate; zirconium (IV) iodide; molybdenum (III) bromide; molybdenum (III) chloride; molybdenum (IV) sulfide; iron (III) hydrate; iron (III) phosphate tetrahydrate, iron (III) sulfate pentahydrate, and the like.

In addition to a metal, the metal derived targeting agent comprises one or more complexing agents. A complexing agent is a compound capable of forming a water insoluble coordination complex with the preferred metal. There are several families of suitable complexing agents.

A complexing agent may be selected from the family of iminodiacetic acids of formula (1) wherein $R_1$ is loweralkyl, aryl, arylloweralkyl, or a heterocyclic substituent.

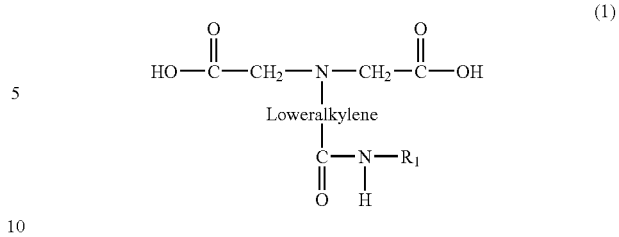

Suitable compounds of formula (1) include:
N-(2,6-diisopropylphenylcarbamoylmethyl)iminodiacetic acid;
N-(2,6-diethylphenylcarbamoylmethyl)iminodiacetic acid;
N-(2,6-dimethylphenylcarbamoylmethyl)iminodiacetic acid;
N-(4-isopropylphenylcarbamoylmethyl)iminodiacetic acid;
N-(4-butylphenylcarbamoylmethyl)iminodiacetic acid;
N-(2,3-dimethylphenylcarbamoylmethyl)iminodiacetic acid;
N-(2,4-dimethylphenylcarbamoylmethyl)iminodiacetic acid;
N-(2,5-dimethylphenylcarbamoylmethyl)iminodiacetic acid;
N-(3,4-dimethylphenylcarbamoylmethyl)iminodiacetic acid;
N-(3,5-dimethylphenylcarbamoylmethyl)iminodiacetic acid;
N-(3-butylphenylcarbamoylmethyl)iminodiacetic acid;
N-(2-butylphenylcarbamoylmethyl)iminodiacetic acid;
N-(4-tertiary butylphenylcarbamoylmethyl)iminodiacetic acid;
N-(3-butoxyphenylcarbamoylmethyl)iminodiacetic acid;
N-(2-hexyloxyphenylcarbamoylmethyl)iminodiacetic acid;
N-(4-hexyloxyphenylcarbamoylmethyl)iminodiacetic acid;
Aminopyrrol iminodiacetic acid;
N-(3-bromo-2,4,6-trimethylphenylcarbamoylmethyl)iminodiacetic acid;
Benzimidazole methyl iminodiacetic acid;
N-(3-cyano-4,5-dimethyl-2-pyrrylcarbamoylmethyl)iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl)iminodiacetic acid and other derivatives of N-(3-cyano-4-methyl-2-pyrrylcarbamoylmethyl)iminodiacetic acid of formula (2),

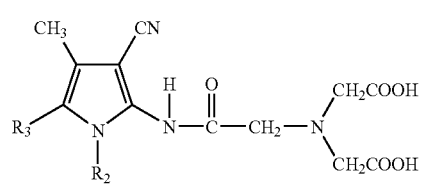

wherein $R_2$ and $R_3$ are the following:
$R_2$ $R_3$
H iso-$C_4H_9$
H $CH_2CH_2SCH_3$
H $CH_2C_6H_4$-p-OH
$CH_3$ $CH_3$
$CH_3$ iso-$C_4H_9$
$CH_3$ $CH_2CH_2SCH_3$
$CH_3$ $C_6H_5$ CH₃ CH₂C₆H₅
CH₃ CH₂C₆H₄-p-OCH₃

Alternatively, the complexing agent may be selected from the family of imino diacid derivatives of formula (3), wherein $R_4$, $R_5$, and $R_6$ are independently selected at each occurrence and may be hydrogen, loweralkyl, aryl, arylloweralkyl, alkoxyloweralkyl, and heterocyclic.

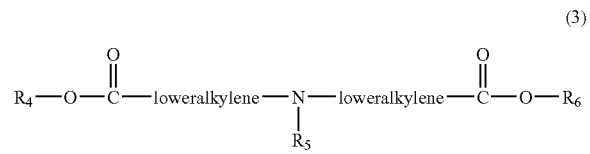

(3)

Suitable compounds of formula (3) include: N'-(2-acetyl-naphthyl)iminodiacetic acid (NAIDA); N'-(2-naphthylmethyl)iminodiacetic acid (NMIDA); iminodicarboxymethyl-2-naphthylketone phthalein complexone; 3 (3: 7a: 12a: trihydroxy-24-norchol anyl-23-iminodiacetic acid; benzimidazole methyl iminodiacetic acid; and N-(5,pregnene-3-p-ol-2-oyl carbamoylmethyl)iminodiacetic acid.

The complexing agent may also be selected from the family of amino acids of formula (4),

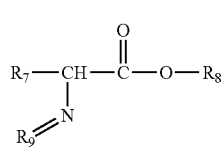

(4)

where $R_7$ is an amino acid side chain; wherein $R_8$ may be loweralkyl, aryl, and arylloweralkyl; and wherein $R_9$ is pyridoxylidene.

Suitable amino acids of the formula (4) are aliphatic amino acids, including, but not limited to: glycine, alanine, valine, leucine, isoleucine; hydroxyamino acids, including serine, and threonine; dicarboxylic amino acids and their amides, including aspartic acid, asparagine, glutamic acid, glutamine; amino acids having basic functions, including lysine, hydroxylysine, histidine, arginine; aromatic amino acids, including phenylalanine, tyrosine, tryptophan, thyroxine; and sulfur-containing amino acids, including cystine and methionine.

The complexing agent may also be selected from amino acid derivatives including, but not limited to (3-alanine-y-amino) butyric acid, O-diazoacetylserine (azaserine), homoserine, ornithine, citrulline, penicillamine and members of the pyridoxylidene class of compounds. Pyridoxylidene compounds include, but are not limited to: pyridoxylidene glutamate; pyridoxylidene isoleucine; pyridoxylidene phenylalanine; pyridoxylidene tryptophan; pyridoxylidene-5-methyl tryptophan; pyridoxylidene-5-hydroxytryptamine; and pyridoxylidene-5-butyltryptamine.

The complexing agent may likewise be selected from the family of diamines of formula (6):

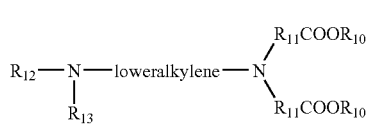

(6)

wherein $R_{10}$ is hydrogen, loweralkyl, or aryl; $R_{11}$ is loweralkylene or arylloweralky; $R_{12}$ and $R_{13}$ are independently selected at each occurrence and may be hydrogen, loweralkyl, alkyl, aryl, arylloweralkyl, acylheterocyclic, toluene, sulfonyl or tosylate.

Examples of suitable diamines of formula (6) include, but are not limited to, ethylenediamine-N,N diacetic acid; ethylenediamine-N,N-bis(-2-hydroxy-5-bromophenyl)acetate; N'-acetylethylenediamine-N,N diacetic acid; N'-benzoyl ethylenediamine-N,N diacetic acid; N'-(p-toluenesulfonyl)ethylenediamine-N,N diacetic acid; N'-(p-t-butylbenzoyl)ethylenediamine-N,N diacetic acid; N'-(benzenesulfonyl) ethylenediamine-N,N diacetic acid; N'-(p-chlorobenzenesulfonyl)ethylenediamine-N,N diacetic acid; N'-(p-ethylbenzenesulfonyl ethylenediamine-N,N diacetic acid; N'-acyl and N'-sulfonyl ethylenediamine-N,N diacetic acid; N'-(p-n-propylbenzenesulfonyl)ethylenediamine-N,N diacetic acid; N'-(naphthalene-2-sulfonyl)ethylenediamine-N,N diacetic acid; and N'-(2,5-dimethylbenzenesulfonyl)ethylenediamine-N,N diacetic acid.

Other, non-limiting examples of complexing compounds or agents include penicillamine; p-mercaptoisobutyric acid; dihydrothioctic acid; 6-mercaptopurine; kethoxal-bis(thiosemicarbazone); Hepatobiliary Amine Complexes, 1-hydrazinophthalazine(hydralazine); sulfonyl urea; Hepatobiliary Amino Acid Schiff Base Complexes; pyridoxylidene glutamate; pyridoxylidene isoleucine; pyridoxylidene phenylalanine; pyridoxylidene tryptophan; pyridoxylidene 5-methyl tryptophan; pyridoxylidene-5-hydroxytryptamine; pyridoxylidene-5-butyltryptamine; tetracycline; 7-carboxy-p-hydroxyquinoline; phenolphthalein; eosin I bluish; eosin I yellowish; verograffin; 3-hydroxy-4-formyl-pyridene glutamic acid; Azo substituted iminodiacetic acid; hepatobiliary dye complexes, such as rose bengal; congo red; bromosulfophthalein; bromophenol blue; toluidine blue; and indocyanine green; hepatobiliary contrast agents, such as iodipamide; and ioglycamic acid; bile salts, such as bilirubin; cholgycyliodohistamine; and thyroxine; hepatobiliary thio complexes, such as penicillamine; p-mercaptoisobutyric acid; dihydrothiocytic acid; 6-mercaptopurine; and kethoxal-bis(thiosemicarbazone); hepatobiliary amine complexes, such as 1-hydrazinophthalazine(hydralazine); and sulfonyl urea; hepatobiliary amino acid Schiff Base complexes, including pyridoxylidene-5-hydroxytryptamine; and pyridoxylidene-5-butyltryptamine; hepatobiliary protein complexes, such as protamine; ferritin; and asialo-orosomucoid; and asialo complexes, such as lactosaminated albumin; immunoglobulins, G, IgG; and hemoglobin.

Addition of Therapeutic Agents

As noted previously, in certain embodiments, one or more therapeutic agents may be associated with a constituent of a composition of the present invention. Examples of therapeutic agents include, but are not limited to, insulin, interferon, erythropoietin, parathyroid hormone, serotonin, D- or L-thyroxine, calcitonin, monoclonal antibodies, as well as other therapeutic peptides.

In certain embodiments, a therapeutic agent such as insulin is associated with a constituent of a composition of the present invention. In one embodiment, association is achieved via addition of a low molarity solution of insulin to an aqueous solution of constituents. In this embodiment, the number of lipid molecules involved in the assembly of the constituents far surpasses the number of molecules of insulin interlaced and/or combined either on or within the constituents' matricies. This high ratio of constituents to insulin minimizes the molecular interactions between insulin and the constituents, insuring that the self-assembly and self-organization process of the constituents of the composition of the present invention are not disrupted. This high ratio facilitates the formation of a stable constituent/insulin association.

Without wishing to be bound by a particular theory, it is believed that the quantity of therapeutic agent(s) associated with a constituent of a composition of the present invention appears to be a function of loading time and lipid concentration. As the lipid component concentration in aqueous media is increased, additional therapeutic agents associate with a constituent of a composition of the present invention. The time required for loading the therapeutic agent may be anywhere from several hours to about one week.

The low concentration of therapeutic agent relative to the concentration of the constituents of the composition of the present invention is unique among lipid particle delivery systems. Typically, liposome or liposome-like delivery systems have employed a much larger quantity of therapeutic agent. The efficacy this embodiment of the present combination indicates that it is possible to utilize less therapeutic agent while still obtaining a pharmacologically desirable result in the patient. This embodiment of the invention therefore provides an advantageous therapeutic option.

In other embodiments the addition of a higher concentration of therapeutic agent may be both desirable and advantageous. The constituent members of a composition of the present invention are capable of associating with, and tolerating, higher molarity solutions of any given therapeutic agent.

A diagrammatic example of an embodiment of a constituent of a composition of the present invention is depicted in FIG. 1. FIG. 1 illustrates a constituent/HTM/insulin construct. Insulin molecules bind to the surface of the constituent via non-covalent electrostatic interactions.

Serotonin, like insulin, may also be delivered to the liver utilizing a constituent/HTM complex according to the invention. Serotonin acts jointly with insulin at the level of the liver to activate hepatic glucose storage during a portal (oral) glucose load. In order to achieve the desired effect, serotonin must be delivered to the liver. Non-targeted serotonin, introduced via injection or oral delivery in pharmacologically acceptable doses cannot effectively induce the desired activity. Therefore, an embodiment of the invention comprising a constituent/HTM/serotonin construct provides a highly desirable delivery mechanism for this important gluco-regulatory hormone. In an embodiment of the invention designed for the delivery of serotonin, the lipid components selected to form the constituents of the composition include approximately 62 mole percent, 1,2-distearoyl-sn-glycero-3-phosphocholine, approximately 22 mole percent dihexadecyl phosphate, approximately 16 mole percent cholesterol and about 1 mole percent of a targeting agent.

Calcitonin is a hormone that regulates bone metabolism. Due to the high prevalence of diseases such as osteoporosis, an oral formulation of this hormone is highly desirable. Presently calcitonin is only deliverable via injection. In an embodiment of the invention designed for the delivery of calcitonin, the lipid components selected to form the constituents of the composition including calcitonin include approximately 62 mole percent, 1,2-distearoyl-sn-glycero-3-phosphocholine, approximately 22 mole percent dihexadecyl phosphate, and approximately 16 mole percent cholesterol.

Stability

Although constituent members of a composition of the present invention are formulated in aqueous media, the constituent members of the composition do not exhibit long term stability in water. Specifically, water aids hydrolysis of any acyl chains present in any of the lipid components of the compositional constituents. The aqueous environment also allows for the ready oxidation of any unsaturated acyl chains present in any of the lipid components. In a preferred embodiment of the present invention, the constituents of the composition of the present invention may be protected for long term storage via interaction with a proteoglycan such as a modified collagen, known generically as dry granulated gelatin. Dry granulated gelatin, when contacted with an aqueous suspension of constituents, reacts with water, stabilizes the constituents, and forms a composition of the present invention.

The reaction of dried granulated gelatin with an aqueous suspension of constituents of a composition of the present invention results in a semi-solid colloidal gel that shields the constituents from direct interaction with water. Any water not associated with gelatin is slowly evaporated via refrigerated storage at about 2° to about 8° C. This results in a pellet like "dry" constituent/gelatin complex which is the composition of the invention. In the composition, the constituent elements are partially dehydrated in a reversible manner and sequestered by the proteinaceous lattice of dry gelatin. This sequestration is enabled by structured water, structured lipid and structured gelatin all interacting through hydrogen bonding, ionic bonding, van der Waal's interactions, and hydrophobic bonding between the lipid components, water, and protein structures, i.e., insulin. The resulting "dry" pellet is stable for long term storage because the activity of water has been mitigated. These pellets can be further processed to a granulated or free-flowing powder for final capsule filling or tabletting, while maintaining their stability.

Upon oral administration to a patient, the "dry" pellet becomes hydrated and once again assumes a semi-solid colloidal gel state. Upon further exposure to the gastric environment, the gel becomes liquid as gelatin is solubilized. Once the gelatin is completely solubilized, the constituent members of the composition of the invention rehydrate, resulting in the formation of a new suspension of constituents within the gastric environment. The reconstituted constituents may then be absorbed into the portal blood flow.

It is important to realize that the role of gelatin in this aspect of the invention is as an active stabilizer of the composition and not an inert filler as is commonly found in oral formulations of many other pharmaceutical compositions. That said, the additional use of gelatin as an inert filler in addition to the aforementioned use is also contemplated.

Formulations

A formulation of a composition of the invention and therapeutic agent (with or without the targeting agent)—hereinafter "composition"—for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, aqueous suspensions, or emulsions.

A tablet comprising the composition of the present invention, for example, be made by compressing or molding the composition optionally with one or more additional ingredients. Compressed tablets may be prepared by compressing, in a suitable device, the composition in a free-flowing form such as a powder or granular preparation, optionally mixed with one or more of a binder, a lubricant, an excipient, a surface active agent, and a dispersing agent. Molded tablets may be made by molding, in a suitable device, the composition, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the composition. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the composition may be made using a physiologically degradable composition, such as gelatin. Such hard capsules comprise the active ingredient, and may further comprise additional ingredients including, for example, an inert solid diluent such as calcium carbonate, calcium phosphate, kaolin or cellulose acetate hydrogen phthalate.

Soft gelatin capsules comprising the composition may be made using a physiologically degradable composition, such as gelatin.

Liquid formulations of the composition which are suitable for oral administration may be prepared, packaged, and sold either in liquid form or in the form of a dry product intended for reconstitution with water or another suitable vehicle prior to use, subject to the stability limitations disclosed earlier.

Liquid suspensions may be prepared using conventional methods to achieve suspension of the constituents in an aqueous vehicle. Aqueous vehicles include, for example, water and isotonic saline. Oily vehicles may only be used to the extent that such solvents are not incompatible with the constituents of the composition of the present invention. To the extent that an oily suspension is not incompatible with the constituents of the composition of the present invention, an oily suspension may further comprise a thickening agent.

Liquid suspensions may further comprise one or more additional ingredients to the extent that said ingredients do not disrupt the structures of the constituents of the composition of the invention. Examples of additional ingredients include, but are not limited to, suspending agents, dispersing or wetting agents, emulsifying agents, demulcents, preservatives, buffers, salts, flavorings, coloring agents, and sweetening agents.

Known suspending agents include, but are not limited to, sorbitol syrup, sodium alginate, polyvinylpyrrolidone, gum tragacanth, gum acacia, and cellulose derivatives such as sodium carboxymethylcellulose, methylcellulose, hydroxypropylmethylcellulose.

Known emulsifying agents include, but are not limited to, acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin.

Powdered and granular formulations of a pharmaceutical preparation of the invention may be prepared using known methods. Such formulations may be administered directly to a subject, used, for example, to form tablets, to fill capsules, or to prepare an aqueous suspension or solution by addition of an aqueous vehicle thereto. Each of these formulations may further comprise one or more of dispersing or wetting agent, a suspending agent, and a preservative. Additional excipients, such as fillers and sweetening, flavoring, or coloring agents, may also be included in these formulations.

EXPERIMENTAL EXAMPLES

Experiment 1

Administration of Compositions not Containing a Targeting Agent

A composition whose constituent members were created from a mixture of lipid components comprising approximately 62 mole percent 1,2-distearoyl-sn-glycero-3-phosphocholine, approximately 22 mole percent dihexadecyl phosphate, approximately 16 mole percent cholesterol, and no targeting agent was prepared according to the microfluidization procedure generally described herein. A known portion of the lipid component comprised $^{14}C$ labeled phospholipid. Following filtration through a 0.2 micron filter, the average constituent size was less than 100 nm as measured with a Coulter Sub-micron Particle Size Analyzer.

Figure 2:
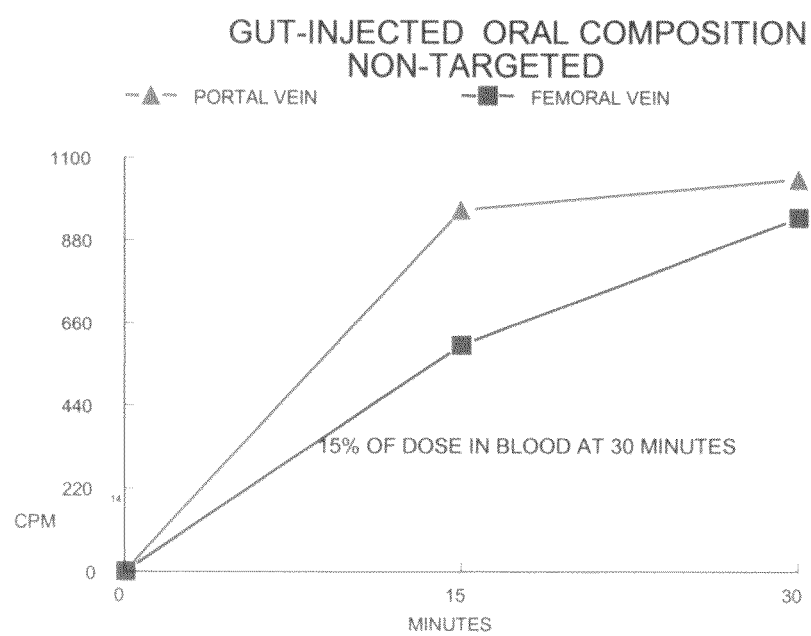
FIG. 2 is a graph depicting the counts of $^{14}C$ radio-labeled phospholipid found in the femoral and portal veins 15 and 30 minutes post injecting radio-labeled composition into the duodenum of a fasted and anesthetized 230 gram rat.
Figure 3:
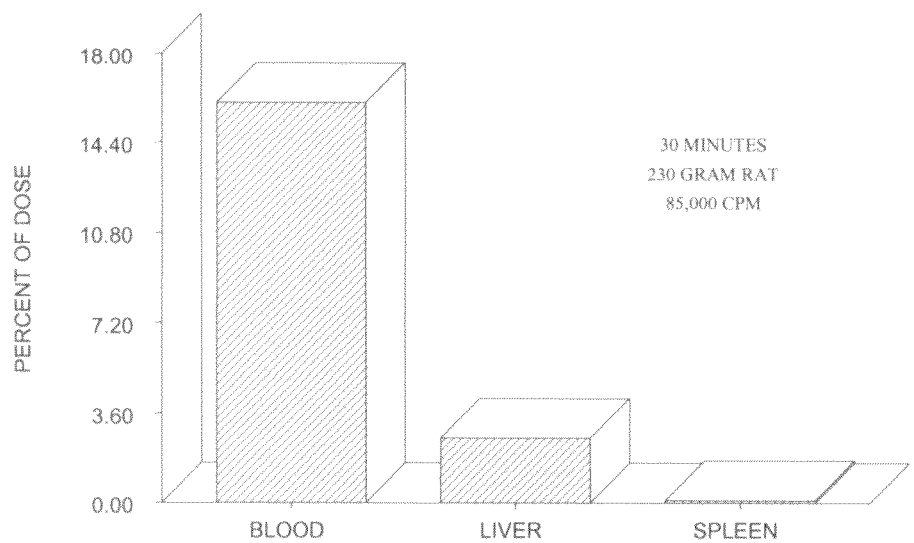
FIG. 3 is a bar graph depicting the distribution of $^{14}C$ radio-labeled phospholipid amongst the blood, liver, and spleen in the rats of FIG. 2, post-sacrifice.

A 10 mg/kg body weight sample of the composition (containing 85,000 cpm of $^{14}C$ radio-label) was then injected into the duodenum of an anesthetized 230 gram fasted, but otherwise normal, rat. Blood was taken from the portal and femoral veins at 15 and 30 minutes post-dosing for counting (FIG. 2). At 30 minutes post-dosing, the rat was sacrificed and representative samples of blood, liver, and spleen were removed for analysis (FIG. 3).

Labeled constituents, as measured by $^{14}C$, were found in both portal and femoral blood of the rat. The portal blood levels of $^{14}C$ labeled constituents were higher than the femoral blood levels (FIG. 2). At 30 minutes post-dosing, approximately 15% of the constituents that were injected into the gut were found in the blood. Approximately 4% of the counts were found in the liver and about 1% were found in the spleen. Considering the relative sizes of the liver and spleen, the splenic uptake was much higher than liver uptake on a weight basis.

Experiment 2

Hepatocyte Targeting

Figure 4:
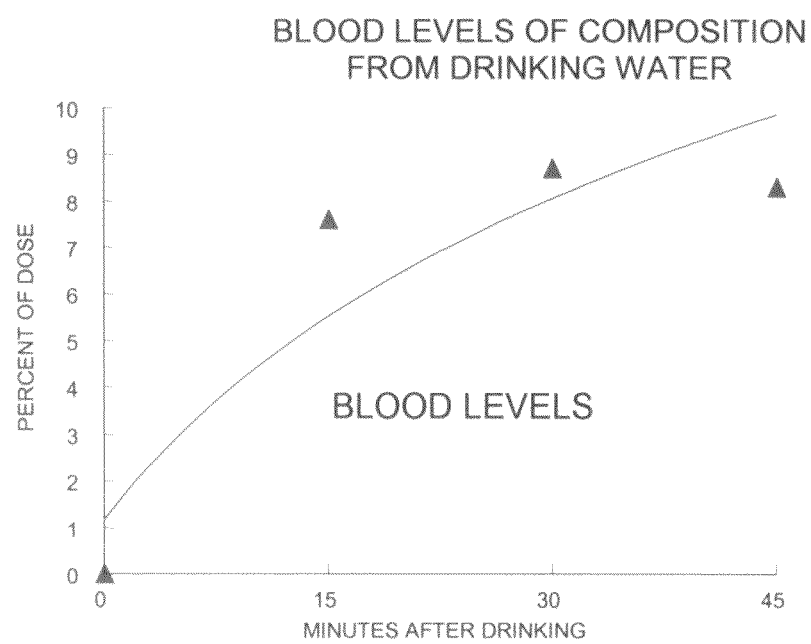
FIG. 4 is a graph depicting the absorption of radio-labeled composition from drinking water at 15, 30, and 45 minutes post-dosing.
Figure 5:
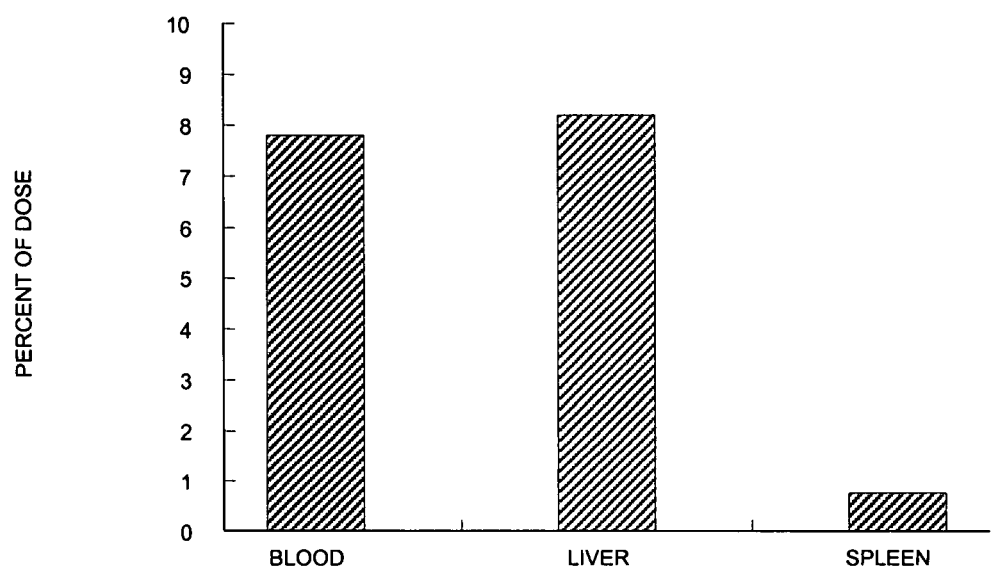
FIG. 5 is a bar graph depicting the distribution of the labeled composition amongst the blood, liver, and spleen in the rats of FIG. 4, post-sacrifice.

To demonstrate the absorption of the composition from the gut, a composition comprising insulin and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and approximately 1 mole percent poly[Cr-bis(N-2,6-diisopropylphenylcarbamoylmethyl iminodiacetic acid)] (wherein a known portion of the phospholipid component comprised $^{14}C$ labeled phospholipid) was prepared as recited in the general preparation disclosed herein. Prior to dosing, the labeled composition to rats, the rats were fasted from food for 24 hours and from water for 4 hours. The fasted rats were then permitted to drink water from a graduated water bottle containing the composition. The drinking water bottle was removed from the cage after 15 minutes, the amount of water ingested from the drinking bottle was measured, and the amount of composition ingested was calculated. The rats' blood was sampled at 15, 30, and 45 minutes and the radiolabel in each sample was counted (FIG. 4). At 45 minutes the rats were sacrificed and the livers were counted for radiolabel (FIG. 5).

As is shown in FIG. 4, approximately 8% of the ingested dose was found in the rats' blood 15 minutes after the water had been removed from the cage. The quantity of constituents in the rats' blood remained constant between 15 and 45 minutes. Liver uptake was approximately 8% at 45 minutes. Splenic uptake at 45 minutes was approximately 1% of the ingested dose (FIG. 5). The total absorption was approximately 17% (including blood, liver, and spleen).

Experiment 3

Hepatocyte Targeting with a Composition in Alloxan-Streptozotocin Treated Mice

Mice used in the present experiment were made diabetic by administering streptozotocin and alloxan. The diabetic animals were then divided into two groups. The control group (11 mice) was orally dosed with regular insulin. The experimental group (7 mice) was orally dosed with a composition comprising insulin and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and approximately 1 mole percent poly[Cr-bis(N-2,6-diisopropylphenylcarbamoylmethyl iminodiacetic acid)] (wherein a known portion of the phospholipid component comprised $^{14}$C labeled phospholipid). Dosing was accomplished utilizing the water bottle dosing method described in Experiment 2.

After being made diabetic, rats in both groups were treated identically over a 7 day period and fed with plain food and plain water. Following this 7 day period, rats in the control group were treated for an additional 7 day experimental period with food and regular insulin in the available drinking water at 0.1 U/ml. Over the same 7 day experimental period, the experimental group was fed regular food with the composition of the invention available in the drinking water at 0.1 U/ml. At the end of each 7-day period, blood glucose was measured in a tail-vein sample of blood by a Beckman Blood Glucose Analyzer.

Figure 6:
FIG. 6 is a graph depicting the efficacy of orally administered insulin in the form of a composition of the invention.

The pharmacologic efficacy of orally administered insulin in the group dosed with the above described composition is shown in FIG. 6. Mice receiving the composition had a statistically significant reduction in blood glucose on day seven ($p<0.01$) compared to mice receiving regular insulin, whose blood glucose was not altered at all.

Example 4

In Vivo Administration of Serotonin

Figure 7:
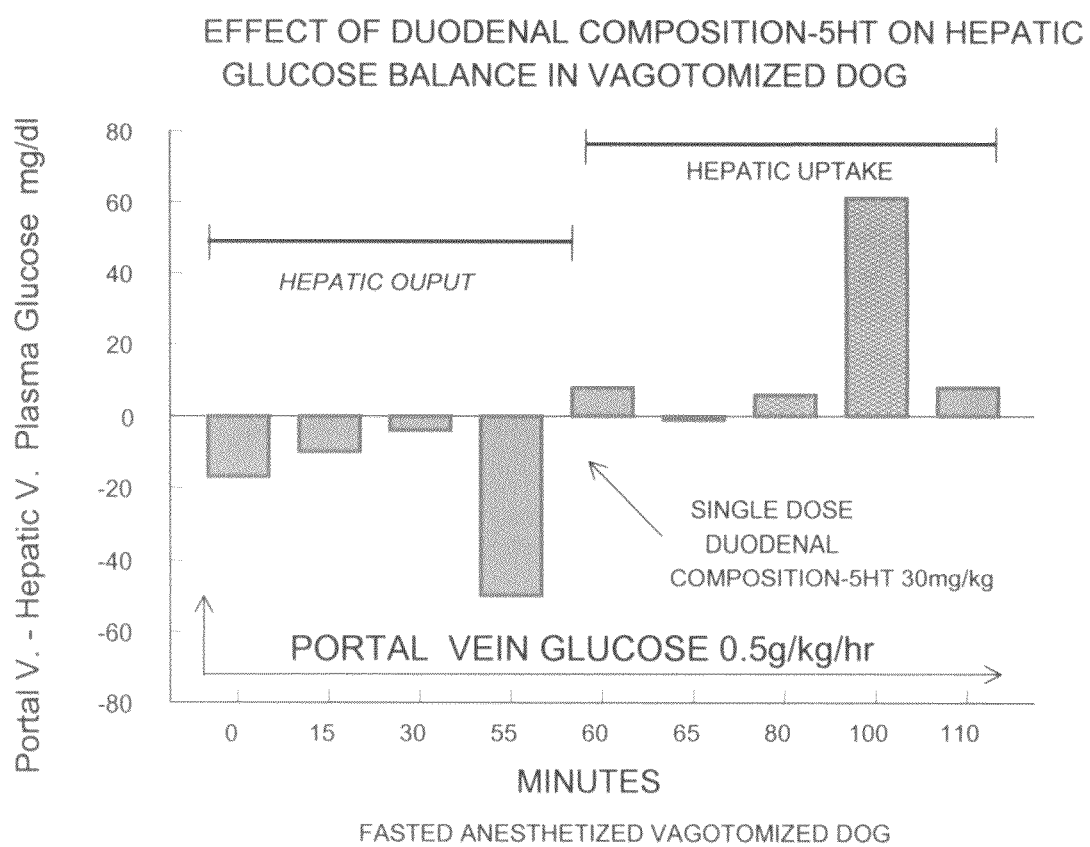
FIG. 7 is a bar graph depicting the efficacy of a composition of the invention (at low dosages), in converting a type 2 diabetic dog from hepatic glucose output to uptake during a portal glucose load.

The hepatic action of a composition comprising serotonin and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and 1 mole percent of poly[Cr-bis(N-2,6-diisopropylphenylcarbamoylmethyl iminodiacetic acid)] was demonstrated in a type 2 diabetic dog (truncal vagotomy). The dog was fasted, and then anesthetized. Blood sampling catheters were placed in the hepatic and portal veins to enable simultaneous blood sampling. Glucose was infused into the portal system at a rate of 0.5 g/kg/hour. Next, the above described composition was administered intraduodenally in a single dose of 30 kg/kg body weight. Results are depicted in FIG. 7 and demonstrate that serotonin (also referred to as 5-hydroxytryptamine or 5-HT), administered intraduodenally as a composition of the invention is effective at low doses in converting a type 2 diabetic dog from hepatic glucose output to uptake during a portal glucose load.

Example 5

In Vivo Administration of Calcitonin

Figure 8:
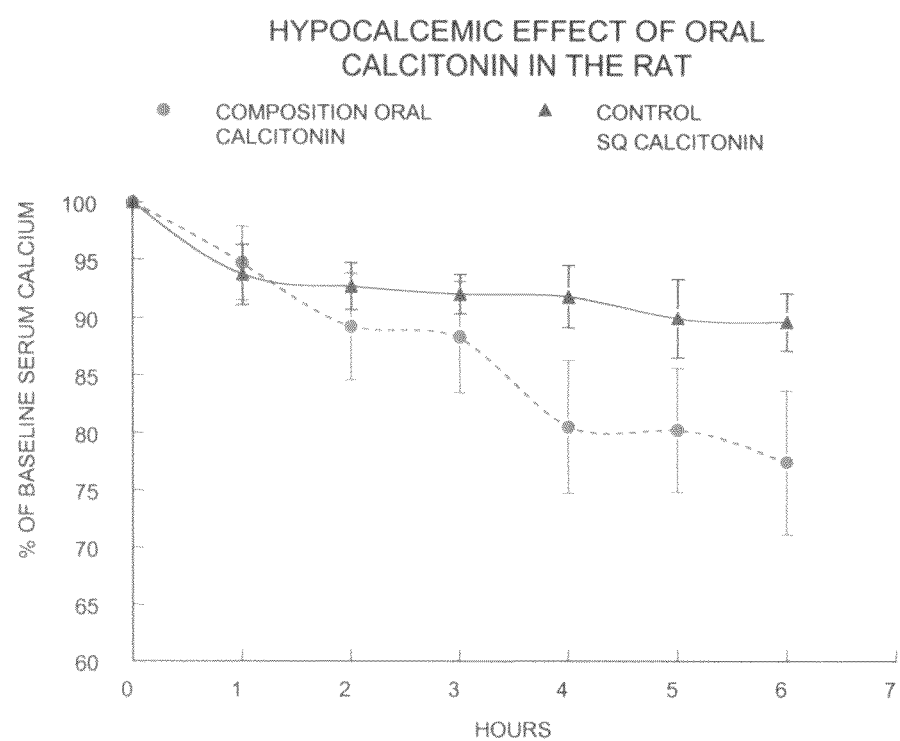
FIG. 8 is a plot of blood calcium levels after the administration of a non-targeted composition of the invention.

Normal, fasted, control rats were given a dose of salmon calcitonin via subcutaneous injection such that an initial 10% reduction in blood calcium was observed. Blood calcium levels were then measured for six hours post injection. An experimental group of rats was given the same effective dose of calcitonin by oral gavage, in the form of a composition comprising calcitonin and constituents generated from a mixture of lipid components comprising approximately 61 mole percent 1,2 distearoyl-sn-glycero-3-phosphocholine, approximately 22 mole percent dihexadecyl phosphate, and approximately 16 mole percent cholesterol. Blood calcium levels were followed for six hours (FIG. 8). A blood calcium reduction of up to 20% was observed in the non-control rats. This difference was statistically significant (FIG. 8).

Example 6

Clinical Trial with Targeted Insulin in Type 2 Diabetes Mellitus Subjects

Capsules containing a composition of the invention were prepared. The composition comprised insulin as the therapeutic agent, gelatin, and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and about 1 mole percent of the sodium salt of Biotin-HDPE. Each capsule contained 2 U of insulin.

Six well characterized Type 2 diabetes patients participated in the controlled study. The patients were maintained on their customary Type 2 oral anti-diabetes therapy. Study participants were also given either placebo capsules or the above described capsules 30 minutes before a 60 gram carbohydrate meal at breakfast, lunch and dinner. Blood samples were drawn at frequent intervals over a 13 hour period and the Incremental Area Under the Curve for the blood glucose values was calculated for each subject.

Figure 10:
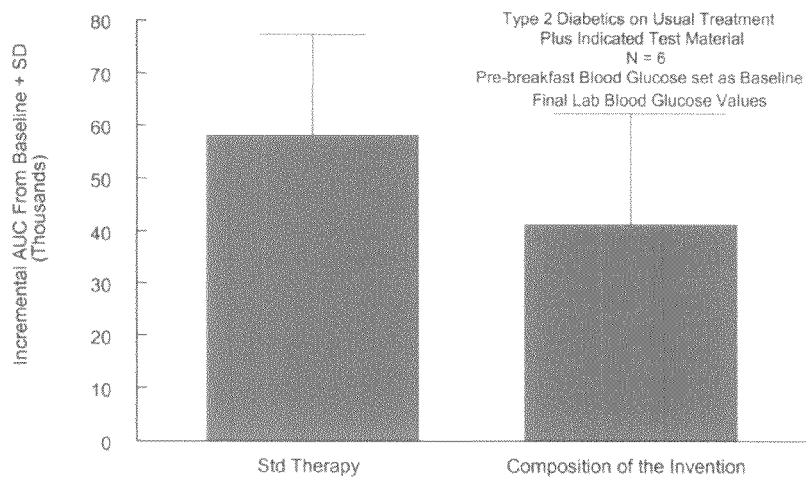
FIG. 10 is a graph of the efficacy of a composition of the invention comprising a biotin targeting agent and insulin at reducing the effects of type 2 diabetes in humans.

At 0.1 U/kg body weight/meal, the same dose that is frequently used with subcutaneous injection of insulin at a given meal, a statistically significant reduction in AUC for each of the three meals was observed. FIG. 10 depicts the results of the trial in graphical format.

Example 7

Insulin Concentration

Insulin U-500 contains 500 units of insulin/ml=0.5 units/1 µl

Add 3.36 ml of U-500 insulin to 70 ml of constituent suspension in 18 mM phosphate buffer @ pH 7.01.

(3,360 μl)*(0.5 units of insulin/μl)=1,680 units of insulin total in 73.36 ml (1,680 units of insulin)/(73.36 ml)=22.9 units of insulin/ml-or-34.35 units of insulin/1.5 ml Load insulin for 21 hours;

Post loading, chromatograph 1.5 ml of sample over a 1.5 cm×25 cm column with Sepharose CL-6B gel equilibrated with 18 mM phosphate buffer @ pH 7.01

0% of free insulin recovered from column; The recovery of 0% of the total loaded insulin implies that 100% of the total "loaded" insulin is associated with a constituent of the composition.

34.35 units of insulin×100%=34.35 units of insulin bound or associated with the constituents of the invention.

Figure 11:
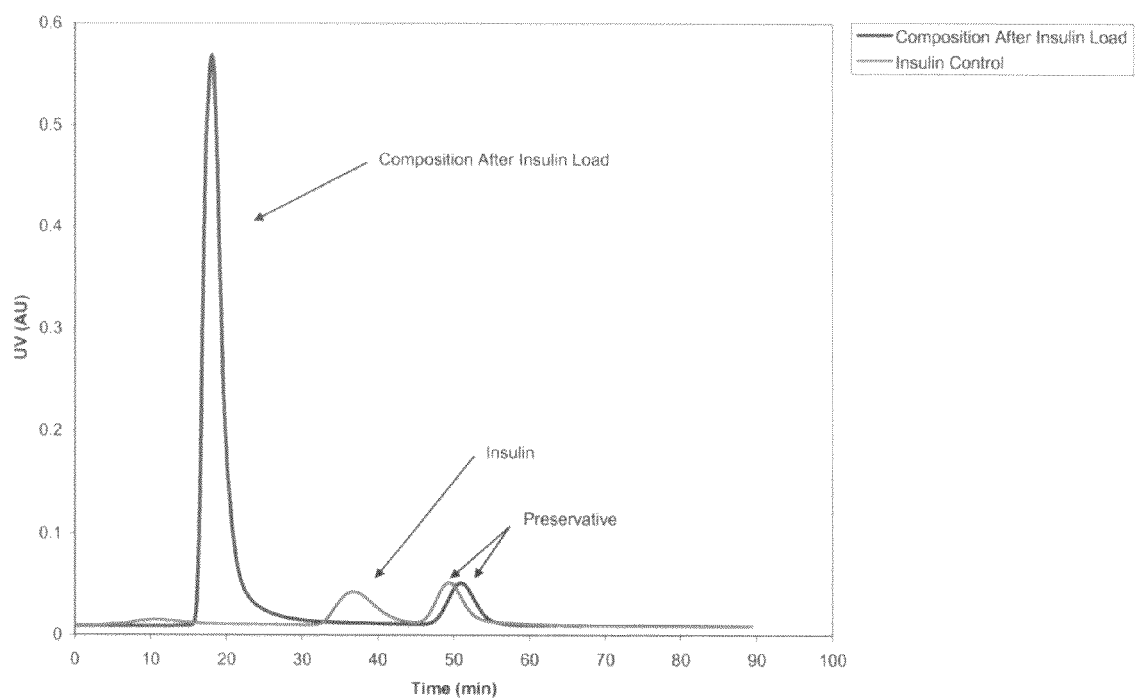
FIG. 11 is a chromatogram of a composition of the invention showing the efficacy of insulin loading.

FIG. 11 depicts the above described chromatography. A trace showing the elution time of free insulin is included for purposes of comparison. As can be seen from the chromatogram, insulin is associated with the constituents of the invention and no free insulin is in solution. A preservative included with insulin does not associate with the constituents of the composition of the invention and is visible in the chromatogram.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An orally bioavailable composition comprising gelatin and additional constituents,
    wherein said constituents comprise a liposome, liposome fragment, and lipid particle,
    wherein said lipid particle comprises at least one lipid component and said liposome or liposome fragment comprises at least two lipid components,
    wherein said composition further comprises insulin and a biotin-derived targeting agent selected from the group consisting of biotin-X-DHPE and biotin-DHPE,
    wherein said gelatin reversibly interacts with one or more of said constituents,
    wherein a percentage ranging from 5% to 50% of said additional constituents exhibits an average diameter equal to or lower than 20 nanometers,
    wherein the lipid components comprise dihexadecyl phosphate, 1,2 distearoyl-sn-glycero-3-phosphocholine, and cholesterol, and
    wherein said composition is orally bioavailable in a mammal.

2. A composition of the invention prepared by a method comprising the steps of:
    a. mixing dihexadecyl phosphate, 1,2 distearoyl-sn-glycero-3-phosphocholine, cholesterol, and a biotin-derived targeting agent selected from the group consisting of biotin-X-DHPE and biotin-DHPE in aqueous media to form a first mixture;
    b. subjecting said mixture to homogenization to form a mixture of liposomes, liposome fragments, and particles;
    c. adding insulin to said mixture of liposomes, liposome fragments, and particles to create a second mixture;
    d. adding said second mixture to gelatin to form a gelatin-associated mixture; and
    e. drying said gelatin-associated mixture, to yield said composition,
    wherein said gelatin reversibly interacts with one or more of said liposomes, liposome fragments, and particles,
    wherein in said composition a percentage ranging from 5% to 50% of said mixture of liposomes, liposome fragments, and particles exhibits an average diameter equal to or lower than 20 nanometers, and
    wherein said composition is orally bioavailable in a mammal.

* * * * *